United States Patent
Trotter

(10) Patent No.: US 7,371,754 B2
(45) Date of Patent: May 13, 2008

(54) TYROSINE KINASE INHIBITORS

(75) Inventor: B. Wesley Trotter, Glenside, PA (US)

(73) Assignee: Merck & Co., Inc., Rahway, NJ (US)

( * ) Notice: Subject to any disclaimer, the term of this patent is extended or adjusted under 35 U.S.C. 154(b) by 458 days.

(21) Appl. No.: 10/510,610

(22) PCT Filed: Apr. 8, 2003

(86) PCT No.: PCT/US03/12457

§ 371 (c)(1),
(2), (4) Date: Oct. 8, 2004

(87) PCT Pub. No.: WO03/086315

PCT Pub. Date: Oct. 23, 2003

(65) Prior Publication Data

US 2005/0227988 A1 Oct. 13, 2005

Related U.S. Application Data

(60) Provisional application No. 60/372,232, filed on Apr. 12, 2002.

(51) Int. Cl.
*A61K 31/498* (2006.01)
*A61K 431/58* (2006.01)
*A61K 31/50* (2006.01)
*C07D 487/04* (2006.01)
*C07D 245/00* (2006.01)
*C07D 487/00* (2006.01)

(52) U.S. Cl. ........................... 514/250; 540/472

(58) Field of Classification Search ............... None
See application file for complete search history.

(56) References Cited

U.S. PATENT DOCUMENTS 4,332,810 A  6/1982  Belanger et al.

FOREIGN PATENT DOCUMENTS

| WO | WO 02/24692 A1 | 3/2002 |
| WO | WO 03 086314 | 10/2003 |
| WO | WO 03 086395 | 10/2003 |

OTHER PUBLICATIONS

Khandwala et al. Endocrine Reviews, 2000, 21(3), 215-244.*
"What is Cancer / General Definition of Cancer". http://training.seer.cancer.gov/module_cancer_disease/units_whatiscancer1_definition.html, accessed Jul. 12, 2007.*
Paradisi et al. Tetrahedron Asymmetry, 2000, 11 (22), 4617-4622. (based on HCAPlus abstract).*
Amirkhosravi et al. Platelets, 1999, 10, 285-292.*
Midgley et al. Expert Opinion in Investigational Drugs, 2001, 10(6), 1011-1019.*
Paradisi et al. Tetrahedron: asymmetry, 2000, 11, 4617-22.*
Belanger, et al., Can. J. Chem., vol. 61, pp. 2177-2182, 1993.
Iddon, et al., J. Chem. Soc. Perkin Trans., vol. 4, pp. 1083-1090, 1990.
Workman, et al., Seminars in Cancer Biology, vol. 3, pp. 369-381, 1992.
Belanger, et al., J. Org. Chem., vol. 47, pp. 4329-4334, 1982.
Paradisi, et al., Tetrahedron: Asymmetry, vol. 11, pp. 4617-4622, 2000.

* cited by examiner

*Primary Examiner*—James O. Wilson
*Assistant Examiner*—Noble Jarrell
(74) *Attorney, Agent, or Firm*—Li Su; David A. Muthard

(57) ABSTRACT

The present invention relates to compounds that are capable of inhibiting, modulating and/or regulating signal transduction of both receptor-type and non-receptor type tyrosine kinases. The compounds of the instant invention possess a core structure that comprises a benzazocine moiety. The present invention is also related to the pharmaceutically acceptable salts, hydrates and stereoisomers of these compounds.

4 Claims, No Drawings

TYROSINE KINASE INHIBITORS

PRIORITY CLAIM

This application is a § 371 application of PCT/US03/12457 that was filed on Apr. 8, 2003, which claims priority from the U.S. Provisional Application No. 60/372,232, that was filed on Apr. 12, 2002 and is now abandoned.

BACKGROUND OF THE INVENTION

Protein kinases (PKs) are enzymes that catalyze the phosphorylation of hydroxy groups on tyrosine, serine and threonine residues of proteins. The consequences of this seemingly simple activity are staggering; cell growth, differentiation and proliferation; i.e., virtually all aspects of cell life, in one way or another depend on PK activity. Furthermore, abnormal PK activity has been related to a host of disorders, ranging from relatively non life-threatening diseases such as psoriasis to extremely virulent diseases such as glioblastoma (brain cancer). PKs can be broken into two classes, the protein tyrosine kinases (PTKs) and the serine-threonine kinases (STKs).

Certain growth factor receptors exhibiting PK activity are known as receptor tyrosine kinases (RTKs). They comprise a large family of transmembrane receptors with diverse biological activity. As present, at least nineteen (19) distinct subfamilies of RTKs have been identified. One RTK subfamily contains the insulin receptor (IR), insulin-like growth factor I receptor (IGF-1R) and insulin receptor related receptor (IRR). IR and IGF-1R interact with insulin, IGF-I and IGF-II to activate a hetero-tetramer composed of two entirely extracellular glycosylated α subunits and two β subunits which cross the cell membrane and which contain the tyrosine kinase domain. The Insulin-like Growth Factor-1 Receptor (IGF-1R), and its ligands, IGF-1 and IGF-2, are abnormally expressed in numerous tumors, including, but not limited to, breast, prostate, thyroid, lung, hepatoma, colon, brain, neuroendocrine, and others.

A more complete listing of the known RTK subfamilies is described in Plowman et al., KN&P, 1994, 7(6):334-339 which is incorporated by reference, including any drawings, as if fully set forth herein.

In addition to the RTKs, there also exists a family of entirely intracellular PTKs called "non-receptor tyrosine kinases" or "cellular tyrosine kinases." This latter designation, abbreviated "CTK", will be used herein. CTKs do not contain extracellular and transmembrane domains. At present, over 24 CTKs in 11 subfamilies (Src, Frk, Btk, Csk, Abl, Zap70, Fes, Fps, Fak, Jak and Ack) have been identified. The Src subfamily appears so far to be the largest group of CTKs and includes Src, Yes, Fyn, Lyn, Lck, Blk, Hck, Fgr and Yrk. For a more detailed discussion of CTKS, see Bolen, Oncogene, 1993, 8:2025-2031, which is incorporated by reference, including any drawings, as if fully set forth herein.

RTKs, CTKs and STKs have all been implicated in a host of pathogenic conditions including significantly, cancer. Other pathogenic conditions, which have been associated with PTKs include, without limitation, psoriasis, hepatic cirrhosis, diabetes, atherosclerosis, angiogenesis, restenosis, ocular diseases, rheumatoid arthritis and other inflammatory disorders, autoimmune diseases and a variety of renal disorders.

SUMMARY OF THE INVENTION

The present invention relates to compounds that are capable of inhibiting, modulating and/or regulating signal transduction of both receptor-type and non-receptor type tyrosine kinases. The compounds of the instant invention possess a core structure that comprises a benzazocine moiety. The present invention is also related to the pharmaceutically acceptable salts and stereoisomers of these compounds.

DETAILED DESCRIPTION OF THE INVENTION

The compounds of this invention are useful in the inhibition of kinases and are illustrated by a compound of Formula I:

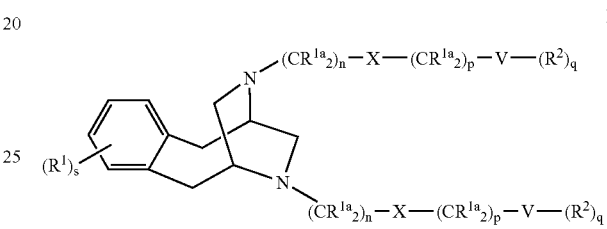

wherein
$R^{1a}$ is independently selected from
  1) H,
  2) unsubstituted or substituted $C_1$-$C_6$ alkyl, and
  3) $OR^4$;
$R^{1b}$ is independently selected from
  1) H, and
  2) unsubstituted or substituted $C_1$-$C_6$ alkyl;
X is independently selected from
  1) a bond,
  2) C(O),
  3) O,
  4) $NR^4$,
  5) $S(O)_m R^4$,
  6) $C(O)OR^4$, and
  7) $C(O)N(R^4)_2$;
$R^1$ is independently selected from
  1) H,
  2) halo,
  3) $OR^4$,
  4) $NO_2$,
  5) —$S(O)_m R^4$,
  6) CN
  7) unsubstituted or substituted $C_1$-$C_{10}$ alkyl,
  8) unsubstituted or substituted aryl,
  9) unsubstituted or substituted $C_2$-$C_6$ alkenyl,
  10) unsubstituted or substituted $C_3$-$C_{10}$ cycloalkyl,
  11) unsubstituted or substituted $C_2$-$C_6$ alkynyl,
  12) unsubstituted or substituted heterocycle,
  13) —$C(O)R^4$,
  14) $C(O)OR^4$,
  15) $C(O)N(R^4)_2$,
  16) $S(O)_m N(R^4)_2$, and
  17) $N(R^4)_2$;
V is independently selected from
  1) H,
  2) $CF_3$, 3) aryl,
4) heterocycle, and
5) $C_3$-$C_{10}$ cycloalkyl;

$R^2$ is independently selected from
1) H,
2) unsubstituted or substituted $C_1$-$C_{10}$ alkyl,
3) —$(CR^{1b})_tOR^4$,
4) Halo,
5) CN,
6) $NO_2$,
7) $CF_3$,
8) —$(CR^{1b})_tN(R^4)_2$,
9) —$C(O)OR^4$,
10) —$C(O)R^4$,
11) —$S(O)_2R^4$,
12) —$(CR^{1b})_tNR^4(CR^{1b})_tR^5$,
13) —$(CR^{1b})_tS(O)_mNR^4$,
14) —$C(O)OR^4R^5$,
15) —$NR^4C(O)R^4$,
16) unsubstituted or substituted aryl, and
17) unsubstituted or substituted heterocycle;

$R^4$ is independently selected from
1) H,
2) unsubstituted or substituted $C_1$-$C_{10}$ alkyl,
3) unsubstituted or substituted $C_3$-$C_{10}$ cycloalkyl,
4) unsubstituted or substituted aryl,
5) unsubstituted or substituted heterocycle, and
6) $CF_3$;

$R^5$ is independently selected from
1) unsubstituted or substituted aryl, and
2) unsubstituted or substituted heterocycle;

m is independently 0, 1 or 2;
n is 0 to 6;
p is 0 to 6;
q is 0 to 6, provided that when V is H or $CF_3$, q is 0; and
s is 0 to 16;
t is independently 0 to 6;

or a pharmaceutically acceptable salt or stereoisomer thereof.

A second embodiment of the instant invention is a compound of Formula I, as described above, wherein $R_{1b}$, $R^4$, $R^5$ and variables m, n, p, q and t are as defined above and:

$R^{1a}$ is independently selected from
1) H, and
2) unsubstituted or substituted $C_1$-$C_6$ alkyl;

X is independently selected from
1) a bond,
2) —$C(O)R^4$, and
3) $C(O)$;

$R^1$ is independently selected from
1) H,
2) halo,
3) $OR^4$,
4) $N(R^4)_2$,
5) $NO_2$, and
6) unsubstituted or substituted $C_1$-$C_{10}$ alkyl;

V is independently selected from
1) H,
2) $CF_3$,
3) aryl, and
4) heterocycle;

$R^2$ is independently selected from
1) H,
2) unsubstituted or substituted $C_1$-$C_{10}$ alkyl,
3) —$(CR^{1b})_tOR^4$,
4) Halo,
5) CN,
6) $NO_2$,
7) $CF_3$,
8) —$(CR^{1b})_tN(R^4)_2$,
9) —$C(O)OR^4$,
10) —$(CR^{1b})_tS(O)_mNR^4$,
11) —$(CR^{1b})_tNR^4(CR^{1b})_tR^5$,
12) —$C(O)OR^4R^5$, and
13) —$NR^4C(O)R^4$;

s is 0 to 6;

or a pharmaceutically acceptable salt or stereoisomer thereof.

A further embodiment of the second embodiment is a compound of Formula I, as described above, wherein $R_{1b}$, X, $R^1$, $R^2$, $R^4$, $R^5$ and variables m, s and t are as defined above and:

$R_{1a}$ is independently selected from
1) H, and
2) unsubstituted or substituted $C_1$-$C_6$ alkyl;

V is independently selected from
1) aryl, and
2) heterocycle;

n is 0 to 3;
p is 0 to 3;
q is 0 to 3;

or a pharmaceutically acceptable salt or stereoisomer thereof.

Examples of compounds of the instant invention include
3-(3-bromobenzyl)-11-methyl-1,2,3,4,5,6-hexahydro-5,2-(epiminomethano)-3-benzazocine;
3-(3-bromobenzyl)-1,2,3,4,5,6-hexahydro-5,2-(epiminomethano)-3-benzazocine;
3,11-bis(3-bromobenzyl)-1,2,3,4,5,6-hexahydro-5,2-(epiminomethano)-3-benzazocine;
11-acetyl-3-(3-bromobenzyl)-1,2,3,4,5,6-hexahydro-5,2-(epiminomethano)-3-benzazocine;

or a pharmaceutically acceptable salt or stereoisomer thereof.

Further examples of compounds of the instant invention include
3-(3-bromobenzyl)-11-methyl-1,2,3,4,5,6-hexahydro-5,2-(epiminomethano)-3-benzazocinium dichloride;
3-(3-bromobenzyl)-1,2,3,4,5,6-hexahydro-5,2-(epiminomethano)-3-benzazocinium dichloride;
3,11-bis(3-bromobenzyl)-1,2,3,4,5,6-hexahydro-5,2-(epiminomethano)-3-benzazocinium dichloride;
11-acetyl-3-(3-bromobenzyl)-1,2,3,4,5,6-hexahydro-5,2-(epiminomethano)-3-benzazocinium trifluoroacetate;

or the free form or stereoisomers thereof.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual enantiomers and diastereomers, with all possible stereoisomers and mixtures thereof, including optical isomers, being included in the present invention. In addition, the compounds disclosed herein may exist as tautomers and both tautomeric forms are intended to be encompassed by the scope of the invention, even though only one tautomeric structure is depicted.

When any variable (e.g. aryl, heterocycle, $R^1$, $R^a$ etc.) occurs more than one time in any substituent, its definition on each occurrence is independent at every other occurrence.

Also, combinations of substituents and variables are permissible only if such combinations result in stable compounds.

Lines drawn into the ring systems from substituents (such as from $R^2$, $R^3$, etc.) indicate that the indicated bond may be attached to any of the substitutable ring carbon atoms or heteroatoms, including the carbon atom or heteroatom that is the point of attachment. If the ring system is polycyclic, such as

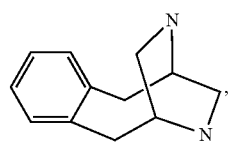

it is intended that the bond may be attached to any of the suitable carbon atoms or heteroatoms of any ring.

It is intended that moiety A, as illustrated in Formula I,

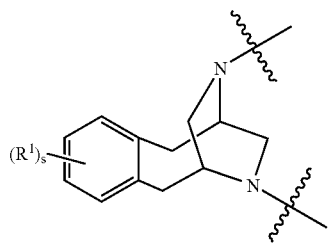

could also be represented as

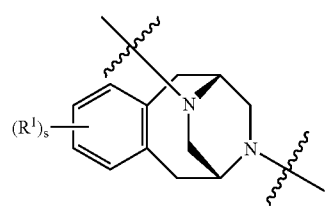

It is also intended that either of the above representations for moiety A could be further illustrated as follows:

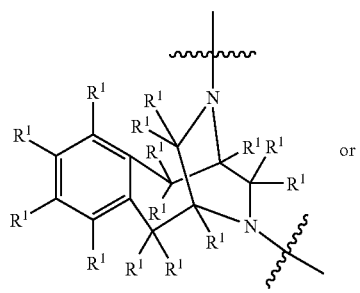

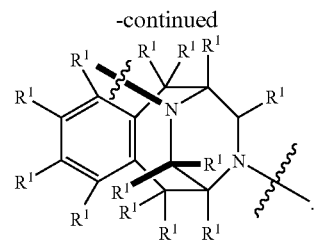

It should be noted that moiety A:

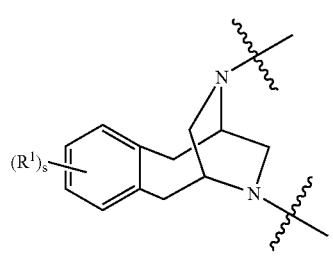

is an enantiomer of

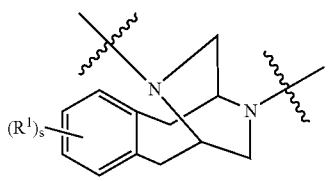

and therefore moiety A and moiety B are stereoisomers. It should also be noted that moiety B could be represented as

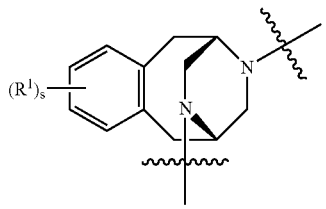

and can be subsituted in a similar manner as illustrated for moiety A.

Additionally, the following structure

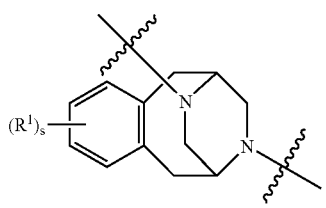

represents a racemic mixture of moiety A and moiety B.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

As used herein, "alkyl" is intended to include both branched, straight-chain, and cyclic saturated aliphatic hydrocarbon groups having the specified number of carbon atoms. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, propyl, isopropyl, butyl, t-butyl, pentyl, hexyl, heptyl, octyl, nonyl, decyl, adamantyl, and so on.

"Cycloalkyl" as used herein is intended to include non-aromatic cyclic hydrocarbon groups, having the specified number of carbon atoms, which may or may not be bridged or structurally constrained. Examples of such cycloalkyls include, but are not limited to, cyclopropyl, cyclobutyl, cyclopentyl, cyclohexyl, adamantyl, cyclooctyl, cycloheptyl, tetrahydro-naphthalene, methylenecylohexyl, and the like. As used herein, examples of "$C_3$-$C_{10}$ cycloalkyl" may include, but are not limited to:

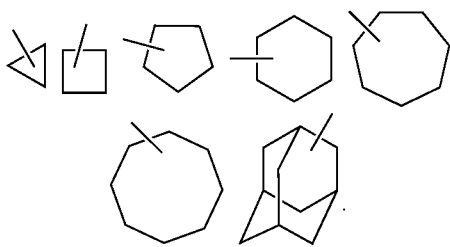

As used herein, the term "alkoxy" represents an alkyl group of indicated number of carbon atoms attached through an oxygen bridge.

If no number of carbon atoms is specified, the term "alkenyl" refers to a non-aromatic hydrocarbon radical, straight, branched or cyclic, containing from 2 to 10 carbon atoms and at least one carbon to carbon double bond. Preferably one carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight, branched or cyclic portion of the alkenyl group may contain double bonds and may be substituted if a substituted alkenyl group is indicated.

The term "alkynyl" refers to a hydrocarbon radical straight, branched or cyclic, containing from 2 to 10 carbon atoms and at least one carbon to carbon triple bond. Up to 3 carbon-carbon triple bonds may be present. Thus, "$C_2$-$C_6$ alkynyl" means an alkynyl radical having from 2 to 6 carbon atoms. Alkynyl groups include ethynyl, propynyl and butynyl. As described above with respect to alkyl, the straight, branched or cyclic portion of the alkynyl group may contain triple bonds and may be substituted if a substituted alkynyl group is indicated.

As used herein, "aryl" is intended to mean any stable monocyclic or bicyclic carbon ring of up to 7 atoms in each ring, wherein at least one ring is aromatic. Examples of such aryl elements include phenyl, naphthyl, tetrahydronaphthyl, indanyl, indanonyl, biphenyl, tetralinyl, tetralonyl, fluorenonyl, phenanthryl, anthryl, acenaphthyl, tetrahydronaphthyl, and the like.

As appreciated by those of skill in the art, "halo" or "halogen" as used herein is intended to include chloro, fluoro, bromo and iodo.

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzodioxolyl, benzotriazolyl, benzothiofuranyl, benzothiazolyl, furanyl, thienyl, benzothienyl, benzofuranyl, benzoquinolinyl, isoquinolinyl, oxazolyl, isoxazolyl, indolyl, pyrazinyl, pyridazinyl, pyridinyl, pyrimidinyl, pyrrolyl, quinolinyl, tetrahydronaphthyl, tetrahydroquinoline, and the like.

The term heterocycle or heterocyclic or heterocyclyl, as used herein, represents a stable 5- to 7-membered monocyclic or stable 8- to 11-membered bicyclic heterocyclic ring which is either saturated or unsaturated, and which consists of carbon atoms and from one to four heteroatoms selected from the group consisting of N, O, and S, and including any bicyclic group in which any of the above-defined heterocyclic rings is fused to a benzene ring. The heterocyclic ring may be attached at any heteroatom or carbon atom which results in the creation of a stable structure. "Heterocycle" or "heterocyclyl" therefore includes the above mentioned heteroaryls, as well as dihydro and tetrahydro analogs thereof. Further examples of "heterocyclyl" include, but are not limited to the following: benzodioxolyl, benzofuranyl, benzofurazanyl, benzoimidazolyl, benzopyranyl, benzopyrazolyl, benzotriazolyl, benzothiazolyl, benzothienyl, benzothiofuranyl, benzothiophenyl, benzothiopyranyl, benzoxazolyl, carbazolyl, carbolinyl, chromanyl, cinnolinyl, diazapinonyl, dihydrobenzofuranyl, dihydrobenzofuryl, dihydrobenzoimidazolyl, dihydrobenzothienyl, dihydrobenzothiopyranyl, dihydrobenzothiopyranylsulfone, dihydrobenzothiophenyl, dihydrobenzoxazolyl, dihydrocyclopentapyridinyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, furyl, furanyl, imidazolyl, imidazolinyl, imidazolidinyl, imidazothiazolyl, imidazopyridinyl, indazolyl, indolazinyl, indolinyl, indolyl, isobenzofuranyl, isochromanyl, isoindolyl, isoindolinyl, isoquinolinone, isoquinolyl, isothiazolyl, isothiazolidinyl, isoxazolinyl, isoxazolyl, methylenedioxybenzoyl, morpholinyl, naphthpyridinyl, oxadiazolyl, oxazolyl, oxazolinyl, oxetanyl, oxoazepinyl, oxadiazolyl, oxodihydrophthalazinyl, oxodihydroindolyl, oxoirnidazolidinyl, oxopiperazinyl, oxopiperdinyl, oxopyrrolidinyl, oxopyrirnidinyl, oxopyrrolyl, oxotriazolyl, piperidyl, piperidinyl, piperazinyl, pyranyl, pyrazinyl, pyrazolyl, pyridazinyl, pyridinonyl, pyridopyridinyl, pyridazinyl, pyridyl, pyrimidinyl, pyrrolyl, pyrrolidinyl, quinazolinyl, quinolinyl, quinolyl, quinolinonyl, quinoxalinyl, tetrahydrocycloheptapyridinyl, tetrahydrofuryl, tetrahydroisoquinolinyl, tetrahydropyranyl, tetrahydroquinolinyl, tetrazolyl, tetrazolopyridyl, thiadiazolyl, thiazolyl, thiazolinyl, thienofuryl, thienyl, triazolyl, azetidinyl, 1,4-dioxanyl, hexahydroazepinyl, and the like. Preferably, heterocycle is selected from oxoazepinyl, benzimidazolyl, diazapinonyl, imidazolyl, oxoimidazolidinyl, indolyl, isoquinolinyl, morpholinyl, piperidyl, piperazinyl, pyridyl, pyrrolidinyl, oxopiperidinyl, oxopyrimidinyl, oxopyrrolidinyl, quinolinyl, tetrahydrofuryl, tetrahydroisoquinolinyl, and thienyl.

As used herein, "aralkyl" is intended to mean an aryl moiety, as defined above, attached through a $C_1$-$C_{10}$ alkyl linker, where alkyl is defined above. Examples of aralkyls include, but are not limited to, benzyl, naphthylmethyl and phenylpropyl.

As used herein, "heterocyclylalkyl" is intended to mean a heterocyclic moiety, as defined below, attached through a $C_1$-$C_{10}$ alkyl linker, where alkyl is defined above. Examples of heterocyclylalkyls include, but are not limited to, pyridylmethyl, imidazolylethyl, pyrrolidinylmethyl, morpholinylethyl, quinolinylmethyl, imidazolylpropyl and the like.

As used herein, the terms "substituted $C_1$-$C_{10}$ alkyl" and "substituted $C_1$-$C_6$ alkoxy" are intended to include the branch or straight-chain alkyl group of the specified number of carbon atoms, wherein the carbon atoms may be substituted with substituents selected from the group which includes, but is not limited to, halo, $C_1$-$C_{20}$ alkyl, $CF_3$, $NH_2$, $N(C_1$-$C_6$ alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

As used herein, the terms "substituted $C_3$-$C_{10}$ cycloalkyl", "substituted aryl", "substituted heterocycle", "substituted aralkyl" and "substituted heterocyclylalkyl" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, $CF_3$, $NH_2$, $N(C_1$-$C_6$alkyl$)_2$, $NO_2$, oxo, CN, $N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, ($C_0$-$C_6$ alkyl)S(O)$_{0-2}$($C_0$-$C_6$alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$ alkyl)O ($C_1$-$C_6$ alkyl)-, ($C_0$-$C_6$ alkyl)C(O)$_{1-2}$ ($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

Preferably, V is independently selected from aryl or heterocycle.

Preferably, $R^1$ is independently selected from H, unsubstituted or substituted $C_1$-$C_{10}$ alkyl, $N(R^4)_2$, $NO_2$, $OR^4$, halo, —C(O)$R^4$, C(O)O$R^4$, and C(O)N($R^4)_2$. More preferably, $R^1$ is independently selected from H, unsubstituted or substituted $C_1$-$C_{10}$ alkyl, $N(R^4)_2$, $NO_2$, $OR^4$, and halo. Most preferably, $R^1$ is independently selected from H, unsubstituted or substituted $C_1$-$C_{10}$ alkyl, and halo.

Preferably, $R^2$ is independently selected from H, unsubstituted or substituted $C_1$-$C_{10}$ alkyl, —(CR$^{1b}$)$_r$OR$^4$, Halo, CN, $NO_2$, $CF_3$, —(CR$^{1b}$)$_r$N(R$^4)_2$, —C(O)OR$^4$, —C(O)R$^4$, —(CR$^{1b}$)$_r$NR$^4$(CR$^{1b}$)$_r$R$^5$, —(CR$^{1b}$)$_r$S(O)$_m$NR$^4$, —C(O)OR$^4$R$^5$, and —NR$^4$C(O)R$^4$. More preferably, $R^2$ is independently selected from H, unsubstituted or substituted $C_1$-$C_{10}$ alkyl, —(CR$^{1b}$)$_r$OR$^4$, Halo, $NO_2$, $CF_3$, and —(CR$^{1b}$)$_r$N (R$^4)_2$. Most preferably, $R^2$ is independently selected from H, unsubstituted or substituted $C_1$-$C_{10}$ alkyl, and halo.

Preferably, X is independently selected from a bond, C(O), or O. Most preferably, X is a bond.

Preferably, n, p and q are independently 0, 1, 2, 3 or 4. More preferably, n and p are independently 0 or 1.

It is intended that the definition of any substituent or variable (e.g., $R^1$, $R^{1a}$, n, etc.) at a particular location in a molecule be independent of its definitions elsewhere in that molecule. Thus, —N(R$^4)_2$ represents —NHH, —NHCH$_3$, —NHC$_2$H$_5$, etc. It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials.

For use in medicine, the salts of the compounds of Formula I will be pharmaceutically acceptable salts. Other salts may, however, be useful in the preparation of the compounds according to the invention or of their pharmaceutically acceptable salts. When the compound of the present invention is acidic, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, N, N$^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The preparation of the pharmaceutically acceptable salts described above and other typical pharmaceutically acceptable salts is more fully described by Berg et al., "Pharmaceutical Salts," J. Pharm. Sci., 1977:66:1-19.

Included in the instant invention is the free form of compounds of Formula I, as well as the pharmaceutically acceptable salts and stereoisomers thereof. Some of the specific compounds exemplified herein are the protonated salts of amine compounds. The term "free form" refers to the amine compounds in non-salt form. The encompassed pharmaceutically acceptable salts not only include the salts exemplified for the specific compounds described herein, but also all the typical pharmaceutically acceptable salts of the free form of compounds of Formula I. The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

Abbreviations, which may be used in the description of the chemistry and in the Examples that follow, include:
$Ac_2O$ Acetic anhydride;
AcOH Acetic acid;
AIBN 2,2'-Azobisisobutyronitrile;
BINAP 2,2'-Bis(diphenylphosphino)-1,1' binaphthyl;
Bn Benzyl;
BOC/Boc tert-Butoxycarbonyl;
BSA Bovine Serum Albumin;
CAN Ceric Ammonia Nitrate;
CBz Carbobenzyloxy;
CI Chemical Ionization;
DBAD Di-tert-butyl azodicarboxylate;
DBU 1,8-Diazabicyclo[5.4.0]undec-7-ene;
DCE 1,2-Dichloroethane;
DCM Dichloromethane;
DIEA N,N-Diisopropylethylamine;
DMAP 4-Dimethylaminopyridine;
DME 1,2-Dimethoxyethane;
DMF N,N-Dimethylformamide;
DMSO Methyl sulfoxide;
DPPA Diphenylphosphoryl azide;
DTT Dithiothreitol;
EDC 1-(3-Dimethylaminopropyl)-3-ethyl-carbodiimide-hydrochloride;
EDTA Ethylenediaminetetraacetic acid;
ES Electrospray;
ESI Electrospray ionization;
$Et_2O$ Diethyl ether;
$Et_3N$ Triethylamine;
EtOAc Ethyl acetate;
EtOH Ethanol;
FAB Fast atom bombardment;
HEPES 4-(2-Hydroxyethyl)-1-piperazineethanesulfonic acid;
HOAc Acetic acid;
HOBT 1-Hydroxybenzotriazole hydrate;
HOOBT 3-Hydroxy-1,2,2-benzotriazin-4(3H)-one;
HPLC High-performance liquid chromatography;
HRMS High Resolution Mass Spectroscopy;
KOtBu Potassium tert-butoxide;
LAH Lithium aluminum hydride;
LCMS Liquid Chromatography Mass Spectroscopy;
LiHMDS Lithium bis(trimethylsilyl)amide;
MCPBA m-Chloroperoxybenzoic acid;
Me Methyl;
MeOH Methanol;
Ms Methanesulfonyl;
MS Mass Spectroscopy;
MsCl Methanesulfonyl chloride;
n-Bu n-butyl;
$n-Bu_3P$ Tri-n-butylphosphine;
NaHMDS Sodium bis(trimethylsilyl)amide;
NBS N-Bromosuccinimide;
$Pd(PPh_3)_4$ Palladium tetrakis(triphenylphosphine);
$Pd_2(dba)_2$ Tris(dibenzylideneacetone)dipalladium (0)
Ph phenyl;
PMSF α-Toluenesulfonyl fluoride;
Py or pyr Pyridine;
PYBOP Benzotriazol-1-yloxytripyrrolidinophosphonium (or PyBOP) hexafluorophosphate;
RPLC Reverse Phase Liquid Chromatography;
RT Room Temperature;
t-Bu tert-Butyl;
TBAF Tetrabutylammonium fluoride;
TBSCl tert-Butyldimethylsilyl chloride;
TFA Trifluoroacetic acid;
THF Tetrahydrofuran;
TIPS Triisopropylsilyl;
TMS Tetramethylsilane;
Tr Trityl; and
Ts Tosyl.

Utility

In another aspect, this present invention relates to a method of modulating the catalytic activity of PKs (protein kinases) in a mammal in need thereof comprising contacting the PK with a compound of Formula I.

As used herein, the term "modulation" or "modulating" refers to the alteration of the catalytic activity of receptor tyrosine kinases (RTKs), cellular tyrosine kinases (CTKs) and serine-threonine kinases (STKs). In particular, modulating refers to the activation of the catalytic activity of RTKs, CTKs and STKs, preferably the activation or inhibition of the catalytic activity of RTKs, CTKs and STKs, depending on the concentration of the compound or salt to which the RTKs, CTKs or STKs is exposed or, more preferably, the inhibition of the catalytic activity of RTKs, CTKs and STKs.

The term "catalytic activity" as used herein refers to the rate of phosphorylation of tyrosine under the influence, direct or indirect, of RTKs and/or CTKs or the phosphorylation of serine and threonine under the influence, direct or indirect, of STKs.

The term "contacting" as used herein refers to bringing a compound of this invention and a target PK together in such a manner that the compound can affect the catalytic activity of the PK, either directly; i.e., by interacting with the kinase itself, or indirectly; i.e., by interacting with another molecule on which the catalytic activity of the kinase is dependent. Such "contacting" can be accomplished "in vitro," i.e., in a test tube, a petri dish or the like. In a test tube, contacting may involve only a compound and a PK of interest or it may involve whole cells. Cells may also be maintained or grown in cell culture dishes and contacted with a compound in that environment. In this context, the ability of a particular compound to affect a PK related disorder; i.e., the $IC_{50}$ of the compound, defined below, can be determined before use of the compounds in vivo with more complex living organisms is attempted. For cells outside the organism, multiple methods exist, and are well known to those skilled in the art, to get the PKs in contact with the compounds including, but not limited to, direct cell microinjection and numerous transmembrane carrier techniques.

The above-referenced PK is selected from the group comprising an RTK, a CTK or an STK in another aspect of this invention. Preferably, the PK is an RTK.

Furthermore, it is an aspect of this invention that the receptor tyrosine kinase (RTK) whose catalytic activity is modulated by a compound of this invention is selected from the group comprising EGF, HBER2, HER3, HER4, IR, IGF-1R, IRR, PDGFRα, PDGFRβ, TrkA, TrkB, TrkC, HGF, CSFIR, C-Kit, C-fms, Flk-1R, Flk4, KDR/Flk-1, Flt-1, FGFR-1R, FGFR-1R, FGFR-3R and FGFR-4R. Preferably, the RTK is preferably, the receptor protein kinase is selected from IR, IGF-1R, or IRR.

In addition, it is an aspect of this invention that the cellular tyrosine kinase whose catalytic activity is modulated by a compound of this invention is selected from the group consisting of Src, Frk, Btk, Csk, Abl, ZAP70, Fes, Fps, Fak, Jak, Ack, Yes, Fyn, Lyn, Lck, Bik, Hck, Fgr and Yrk.

Another aspect of this invention is that the serine-threonine protein kinase whose catalytic activity is modulated by a compound of this invention is selected from the group consisting of CDK2 and Raf.

In another aspect, this invention relates to a method for treating or preventing a PK-related disorder in a mammal in need of such treatment comprising administering to the mammal a therapeutically effective amount of one or more of the compounds described above.

As used herein, "PK-related disorder," "PK driven disorder," and "abnormal PK activity" all refer to a condition characterized by inappropriate (i.e., diminished or, more commonly, exessive) PK catalytic activity, where the particular PK can be an RTK, a CTK or an STK. Inappropriate catalytic activity can arise as the result of either: (1) PK expression in cells which normally do not express PKs; (2) increased PK expression leading to unwanted cell proliferation, differentiation and/or growth; or, (3) decreased PK expression leading to unwanted reductions in cell proliferation, differentiation and/or growth. Excessive-activity of a PK refers to either amplification of the gene encoding a particular PK or its ligand, or production of a level of PK activity which can correlate with a cell proliferation, differentiation and/or growth disorder (that is, as the level of the PK increases, the severity of one or more symptoms of a cellular disorder increase as the level of the PK activity decreases).

"Treat," "treating" or "treatment" with regard to a PK-related disorder refers to alleviating or abrogating the cause and/or the effects of a PK-related disorder.

As used herein, the terms "prevent", "preventing" and "prevention" refer to a method for barring a mammal from acquiring a PK-related disorder in the first place.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The term "treating cancer" or "treatment of cancer" refers to administration to a mammal afflicted with a cancerous condition and refers to an effect that alleviates the cancerous condition by killing the cancerous cells, but also to an effect that results in the inhibition of growth and/or metastasis of the cancer.

The protein kinase-related disorder may be selected from the group comprising an RTK, a CiK or an STK-related disorder in a further aspect of this invention. Preferably, the protein kinase-related disorder is an RTK-related disorder.

In yet another aspect of this invention, the above referenced PK-related disorder may be selected from the group consisting of an EGFR-related disorder, a PDGFR-related disorder, an IGFR-related disorder and a flk-related disorder.

The above referenced PK-related disorder may be a cancer selected from, but not limited to, astrocytoma, basal or squamous cell carcinoma, brain cancer, gliobastoma, bladder cancer, breast cancer, colorectal cancer, chrondrosarcoma, cervical cancer, adrenal cancer, choriocarcinoma, esophageal cancer, endometrial carcinoma, erythroleukemia, Ewing's sarcoma, gastrointestinal cancer, head and neck cancer, hepatoma, glioma, hepatocellular carcinoma, leukemia, leiomyoma, melanoma, non-small cell lung cancer, neural cancer, ovarian cancer, pancreatic cancer, prostate cancer, renal cell carcinoma, rhabdomyosarcoma, small cell lung cancer, thyoma, thyroid cancer, testicular cancer and osteosarcoma in a further aspect of this invention. More preferably, the PK-related disorder is a cancer selected from brain cancer, breast cancer, prostate cancer, colorectal cancer, small cell lung cancer, non-small cell lung cancer, renal cell carcinoma or endometrial carcinoma.

Included within the scope of the present invention is a pharmaceutical composition, which is comprised of a compound of Formula I as described above and a pharmaceutically acceptable carrier. The present invention also encompasses a method of treating or preventing cancer in a mammal in need of such treatment which is comprised of administering to said mammal a therapeutically effective amount of a compound of Formula I. Types of cancers which may be treated using compounds of Formula I include, but are not limited to, astrocytoma, basal or squamous cell carcinoma, brain cancer, gliobastoma, bladder cancer, breast cancer, colorectal cancer, chrondrosarcoma, cervical cancer, adrenal cancer, choriocarcinoma, esophageal cancer, endometrial carcinoma, erythroleukemia, Ewing's sarcoma, gastrointestinal cancer, head and neck cancer, hepatoma, glioma, hepatocellular carcinoma, leukemia, leiomyona, melanoma, non-small cell lung cancer, neural cancer, ovarian cancer, pancreatic cancer, prostate cancer, renal cell carcinoma, rhabdomyosarcoma, small cell lung cancer, thymona, thyroid cancer, testicular cancer and osteosarcoma in a further aspect of this invention. More preferably, the cancer being treated is selected from breast cancer, prostate cancer, colorectal cancer, small cell lung cancer, non-small cell lung cancer, renal cell carcinoma, or endometrial carcinoma.

The above-referenced PK-related disorder may be an IGFR-related disorder selected from diabetes, an autoimmune disorder, Alzheimer's and other cognitive disorders, a hyperproliferation disorder, aging, cancer, acromegaly, Crohn's disease, endometriosis, diabetic retinopathy, restenosis, fibrosis, psoriasis, osteoarthritis, rheumatoid arthritis, an inflammatory disorder and angiogenesis in yet another aspect of this invention.

A method of treating or preventing retinal vascularization which is comprised of administering to a mammal in need of such treatment a therapeutically effective amount of compound of Formula I is also encompassed by the present invention. Methods of treating or preventing ocular diseases, such as diabetic retinopathy and age-related macular degeneration, are also part of the invention. Also included within the scope of the present invention is a method of treating or preventing inflammatory diseases, such as rheumatoid arthritis, psoriasis, contact dermatitis and delayed hypersensitivity reactions, as well as treatment or prevention of bone associated pathologies selected from osteosarcoma, osteoarthritis, and rickets.

Other disorders which might be treated with compounds of this invention include, without limitation, immunological and cardiovascular disorders such as atherosclerosis.

The invention also contemplates the use of the instantly claimed compounds in combination with a second compound selected from the group consisting of:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) angiogenesis inhibitor.

A preferred angiogenesis inhibitor is selected from the group consisting of a tyrosine kinase inhibitor, an inhibitor of epidermal-derived growth factor, an inhibitor of fibroblast-derived growth factor, an inhibitor of platelet derived growth factor, an MMP inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, and an antibody to VEGF. Preferred estrogen receptor modulators are tamoxifen and raloxifene.

Also included in the scope of the claims is a method of treating cancer, which comprises administering a therapeutically effective amount of a compound of Formula I in combination with a compound selected from the group consisting of:
1) an estrogen receptor modulator,
2) an androgen receptor modulator,
3) retinoid receptor modulator,
4) a cytotoxic agent,
5) an antiproliferative agent,
6) a prenyl-protein transferase inhibitor,
7) an HMG-CoA reductase inhibitor,
8) an HIV protease inhibitor,
9) a reverse transcriptase inhibitor, and
10) angiogenesis inhibitor.

And yet another embodiment is the method of treating cancer using the combination discussed above, in combination with radiation therapy.

And yet another embodiment of the invention is a method of treating cancer which comprises administering a therapeutically effective amount of a compound of Formula I in combination with paclitaxel or trastuzumab. The PKs whose catalytic activity is modulated by the compounds of this invention include protein tyrosine kinases of which there are two types, receptor tyrosine kinases (RTKs) and cellular tyrosine kinases (CTKs), and serine-threonine kinases (STKs). RTK-mediated signal transduction, is initiated by extracellular interaction with a specific growth factor (ligand), followed by receptor dimerization (or conformational changes in the case of IR, IGF-1R or IRR), transient stimulation of the intrinsic protein tyrosine kinase activity, autophosphorylation and subsequent phosphorylation of other substrate proteins. Binding sites are thereby created for intracellular signal transduction molecules and lead to the formation of complexes with a spectrum of cytoplasmic signaling molecules that facilitate the appropriate cellular response (e.g., cell division, metabolic effects on the extracellular microenvironment, etc.). See Schlessinger and Ullrich, 1992, Neuron 9:303-391.

It has been shown that tyrosine phosphorylation sites, on growth factor receptors, function as high-affinity binding sites for SH2 (src homology) domains of signaling molecules. Fantl et al., 1992, Cell 69:413-423; Songyang et al., 1994, Mol., Cell. Biol. 14:2777-2785); Songyang et al., 1993, Cell 72:767-778; and Koch et al., 1991, Science 252:668-678. Another signaling molecule domain, which interacts with phosphorylated tyrosines, is termed a PTB domain. Blaikie et al., 1994, J. Biol. Chem. 269:32031-32034; Gustafson et al., 1995, Mol. Cell Biol., 15:2500-25008; Kavanaugh and Williams, 1994, Science 266:1862-1865. Several intracellular substrate proteins that associate with RTKs have been identified. They may be divided into two principal groups: (1) substrates which have a catalytic domain; and (2) substrates which lack such domain, but which serve as adapters and associate with catalytically active molecules. Songyang et al., 1993, Cell 72:767-778. The specificity of the interactions between receptors and SH2 domains of their substrates is determined by the amino acid residues immediately surrounding the phosphorylated tyrosine residue. Differences in the binding affinities between SH2 or PTB domains and the amino acid sequences surrounding the phosphotyrosine residues on particular receptors are consistent with the observed differences in their substrate phosphorylation profiles. Songyang et al., 1993, Cell 72:767-778. These observations suggest that the function of each RTK is determined not only by its pattern of expression and ligand availability, but also by the array of downstream signal transduction pathways that are activated by a particular receptor. Thus, phosphorylation provides an important regulatory step, which determines the selectivity of signaling pathways recruited by specific growth factor receptors, as well as differentiation factor receptors.

STKs, being primarily cytosolic, affect the internal biochemistry of the cell, often as a down-stream response to a PTK event. STKs have been implicated in the signaling process which initiates DNA synthesis and subsequent mitosis leading to cell proliferation.

Thus, PK signal transduction results in, among other responses, cell proliferation, differentiation, growth, metabolism, and cellular mobility. Abnormal cell proliferation may result in a wide array of disorders and diseases, including the development of neoplasia such as carcinoma, sarcoma, glioblastoma and hemangioma, disorders such as leukemia, psoriasis, arteriosclerosis, arthritis and diabetic retinopathy and other disorders related to uncontrolled angiogenesis and/or vasculogenesis.

A precise understanding of the mechanism by which the compounds of this invention inhibit PKs is not required in order to practice the present invention. However, while not hereby being bound to any particular mechanism or theory, it is believed that the compounds interact with the amino acids in the catalytic region of PKs. PKs typically possess a bi-lobate structure wherein ATP appears to bind in the cleft between the two lobes in a region where the amino acids are conserved among PKs. Inhibitors of PKs are believed to bind by non-covalent interactions such as hydrogen bonding, van der Waals forces and ionic interactions in the same general region where the aforesaid ATP binds to the PKs.

The compounds disclosed herein may have utility as in vitro assays for such proteins as well as exhibiting in vivo therapeutic effects through interaction with such proteins.

In another aspect, the protein kinase (PK), the catalytic activity of which is modulated by contact with a compound of this invention, is a protein tyrosine kinase (PTK), more particularly, a receptor protein tyrosine kinase (RTK). Among the RTKs whose catalytic activity can be modulated with a compound of this invention, or salt thereof, are, without limitation, EGF, HER2, HER3, HER4, IR, IGF-1R, IRR, PDGFRα, PDGFRβ, TrkA, TrkB, TrkC, HGF, CSFIR, C-Kit, C-fms, Flk-1R, Flk4, KDR/Flk-1, Flt-1, FGFR-1R, FGFR-2R, FGFR-3R and FGFR-4R. Most preferably, the RTK is selected from IGF-1R.

The protein tyrosine kinase whose catalytic activity is modulated by contact with a compound of this invention, or a salt or a prodrug thereof, can also be a non-receptor or cellular protein tyrosine kinase (CTK). Thus, the catalytic activity of CTKs such as, without limitation, Src, Frk, Btk, Csk, Abl, ZAP70, Fes, Fps, Fak, Jak, Ack, Yes, Fyn, Lyn, Lck, Blk, Hck, Fgr and Yrk, may be modulated by contact with a compound or salt of this invention.

Still another group of PKs which may have their catalytic activity modulated by contact with a compound of this invention are the serine-threonine protein kinases such as, without limitation, CDK2 and Raf.

This invention is also directed to compounds that modulate PK signal transduction by affecting the enzymatic activity of RTKs, CTKs and/or STKs, thereby interfering with the signals transduced by such proteins. More particularly, the present invention is directed to compounds which modulate RTK, CTK and/or STK mediated signal transduction pathways as a therapeutic approach to cure many kinds of solid tumors, including, but not limited to, carcinomas, sarcomas including Kaposi's sarcoma, erythroblastoma, glioblastoma, meningioma, astrocytoma, melonoma and myoblastoma. Treatment or prevention of non-solid tumor cancers such as leukemia are also contemplated by this invention. Indications may include, but are not limited to brain cancers, bladder cancers, ovarian cancers, gastric cancers, pancreatic cancers, colon cancers, blood cancers, breast cancers, prostrate cancers, renal cell carcinomas, lung cancer and bone cancers.

Further examples, without limitation, of the types of disorders related to inappropriate PK activity that the compounds described herein may be useful in preventing, treating and studying, are cell proliferative disorders, fibrotic disorders and metabolic disorders.

As previously mentioned, the Insulin-like Growth Factor-1 Receptor (IGF-1R) belongs to the family of transmembrane tyrosine kinase receptors such as platelet-derived growth factor receptor, the epidermal growth factor receptor, and the insulin receptor. There are two known ligands for the IGF-1R receptor. They are IGF-1 and IGF-2. As used herein, the term "IGF" refers to both IGF-1 and IGF-2. The insulin-like growth factor family of ligands, receptors and binding proteins is reviewed in Krywicki and Yee, *Breast Cancer Research and Treatment*, 22:7-19, 1992.

IGF/IGF-1R driven disorders are characterized by inappropriate or over-activity of IGF/IGF-1R. Inappropriate IGF activity refers to either: (1) IGF or IGF-1R expression in cells which normally do not express IGF or IGF-1R; (2) increased IGF or IGF-1R expression leading to unwanted cell proliferation such as cancer; (3) increased IGF or IGF-1R activity leading to unwanted cell proliferation, such as cancer; and/or over-activity of IGF or IGF-1R. Over-activity of IGF or IGF-1R refers to either an amplification of the gene encoding IGF-1, IGF-2, IGF-1R or the production of a level of IGF activity which can be correlated with a cell proliferative disorder (i.e., as the level of IGF increases the severity of one or more of the symptoms of the cell proliferative disorder increases) the bioavailability of IGF-1 and IGF-2 can also be affected by the presence or absence of a set of IGF binding presence or absence of a set of IGF binding proteins (IGF BPs) of which there are six know. Over activity of IGF/IGF-1R can also result from a down regulation of IGF-2 which contains an IGF-2 binding domain, but no intracellular kinase domain. Examples of IGF/IGF-1R driven disorders include the various IGF/IGF-1R related human malignancies reviewed in Cullen, et al., *Cancer Investigation*, 9(4):443454, 1991, incorporated herein by reference in its entirety, including any drawings. IGF/IGF-1Rs clinical importance and role in regulating osteoblast function is reviewed in Schmid, *Journal of Internal Medicine*, 234:535-542, 1993.

Thus, IGF-1R activities include: (1) phosphorylation of IGF-1R protein; (2) phosphorylation of an IGF-1R protein substrate; (3) interaction with an IGF adapter protein; (4) IGF-1R protein surface expression. Additional IGF-1R protein activities can be identified using standard techniques. IGF-1R activity can be assayed by measuring one or more of the following activities: (1) phosphorylation of IGF-1R; (2) phosphorylation of an IGF-1R substrate; (3) activation of an IGF-1R adapter molecule; and (4) activation of downstream signaling molecules, and/or (5) increased cell division. These activities can be measured using techniques described below and known in the arts.

IGF-1R has been implicated as an absolute requirement for the establishment and maintenance of the transformed phenotype both in vitro and in vivo in several cell types (R. Baserga, *Cancer Research* 55:249-252, 1995). Herbimycin A has been said to inhibit the IGF-1R protein tyrosine kinase and cellular proliferation in human breast cancer cells (Sepp-Lorenzino, et al., 1994, *J. Cell Biochem. Suppl.* 18b:246). Experiments studying the role of IGF-1R in transformation have used antisense strategies, dominant negative mutants, and antibodies to the IGF-1R and have led to the suggestion that IGR-1R may be a preferred target for therapeutic interventions.

IGF-1R, in addition to being implicated in nutritional support and in type-II diabetes, has also been associated with several types of cancers. For example, IGF-1 has been implicated as an autocrine growth stimulator for several tumor types, e.g. human breast cancer carcinoma cells (Arteago et al., J. Clin. Invest., 1989, 84:1418-1423) and small lung tumor cells (Macauley et al., Cancer Res., 1989, 50:2511-2517). In addition, IGF-1, while integrally involved in the normal growth and differentiation of the nervous system, also appears to be an autocrine stimulator of human gliomas. Sandberg-Nordqvist et al., Cancer Res., 1993, 53:2475-2478.

An example of IGF-2's potential involvement in colorectal cancer may be found in the up-regulation of IGF-2 MRNA in colon tumors relative to normal color tissue. (Zhang et al., Science (1997) 276:1268-1272.) IGF-2 may also play a role in hypoxia induced neovascularization of tumors. (Minet et al., Int. J. Mol. Med. (2000) 5:253-259.) IGF-2 may also play a role in tumorigenesis through activation of an insulin receptor isoform-A. IGF-2 activation of insulin receptor isoform-A activates cell survival signaling pathways in cells but its relative contribution to tumor cell growth and survival is unknown at this time. Insulin receptor isoform-A's kinase domain is identical to the standard insulin receptor's. Scalia et al., 2001, J. Cell Biochem. 82:610-618.

The importance of IGF-1R and its ligands in cell types in culture (fibroblasts, epithelial cells, smooth muscle cells, T-lymphocytes, myeloid cells, chondrocytes and osteoblasts (the stem cells of the bone marrow)) is illustrated by the ability of IGF-1 to stimulate cell growth and proliferation. Goldring and Goldring, Eukaryotic Gene Expression, 1991, 1:301-326. In a series of recent publications, Baserga and others suggests that IGF-1R plays a central role in the mechanism of transformation and, as such, could be a preferred target for therapeutic interventions for a broad spectrum of human malignancies. Baserga, Cancer Res., 1995, 55:249-252; Baserga, Cell, 1994, 79:927-930; Coppola et al., Mol. Cell. Biol., 1994, 14:4588-4595; Baserga, Trends in Biotechnology, 1996, 14:150-152; H. M. Khandwala et al., Endocrine Reviews, 21:215-244, 2000. The predominant cancers that may be treated using a compound of the instant invention include, but are not limited to breast cancer, prostate cancer, colorectal cancer, small cell lung cancer, non-small cell lung cancer, renal cell carcinoma, or endometrial carcinoma.

IGF-1 has also been associated with retinal neovascularization. Proliferative diabetes retinopathy has been seen in some patients having high levels of IGF-1. (L. E. Smith et al., Nature Medicine, 1999, 5:1390-1395.)

Compounds of the instant invention may also be useful as anti-aging agents. It has been observed that there is a link between IGF signalling and aging. Experiments have shown that calorie-restricted mammals have low levels of insulin and IGF-1 and have a longer life span. Similar observations have been made for insects as well. (See C. Kenyon, Cell, 2001, 105:165-168; E. Strauss, Science, 2001, 292:4143; K. D. Kimura et al., Science 1997, 277:942-946; M. Tatar et al., Science, 2001, 292:107-110).

STKs have been implicated in many types of cancer including, notably, breast cancer (Cance et al., Int. J. Cancer, 1993, 54:571-77).

The association between abnormal PK activity and disease is not restricted to cancer. For example, RTKs have been associated with diseases such as psoriasis, diabetes mellitus, endometriosis, angiogenesis, atheromatous plaque development, Alzheimer's disease, epidermal hyperproliferation, neurodegenerative diseases, age-related macular degeneration and hemangiomas. For example, EGFR has been indicated in corneal and dermal wound healing. Defects in Insulin-R and IGF-1R are indicated in type-II diabetes mellitus. A more complete correlation between specific RTKs and their therapeutic indications is set forth in Plowman et al., DN&P, 1994,7:334-339.

As noted previously, not only RTKs but CTKs including, but not limited to, src, abl, fps, yes, fyn, lyn, lck, Zap70, blk, hck, fgr and yrk (reviewed by Bolen et al., FASEB J., 1993, 6:3403-3409) are involved in the proliferative and metabolic signal transduction pathway and thus could be expected, and have been shown, to be involved in may PTK-mediated disorders to which the present invention is directed. For example, mutated src (v-src) has been shown to be an oncoprotein (pp60$^{v-src}$) in chicken. Moreover, its cellular homolog, the protooncogene pp60$^{c-src}$ transmits oncogenic signals of many receptors. Over-expression of EGFR or HER$^2$/neu in tumors leads to the constitutive activation of pp60$^{c-src}$, which is characteristic of malignant cells, but absent in normal cells. On the other hand, mice deficient in the expression of c-src exhibit an osteopetrotic phenotype, indicating a key participation of c-src in osteoclast function and a possible involvement in related disorders.

Similarly, Zap70 has been implicated in T-cell signaling which may relate to autoimmune disorders.

STKs have been associated with inflammation, autoimmune disease, immunoresponses, and hyperproliferation disorders such as restenosis, fibrosis, psoriasis, osteoarthritis and rheumatoid arthritis.

PKs have also been implicated in embryo implantation. Thus, the compounds of this invention may provide an effective method of preventing such embryo implantation and thereby be useful as birth control agents.

Finally, both RTKs and CTKs are currently suspected as being involved in hyperimmune disorders.

These and other aspects of the invention will be apparent from the teachings contained herein.

A method for identifying a chemical compound that modulates the catalytic activity of one or more of the above discussed protein kinases is another aspect of this invention. The method involved contacting cells expressing the desired protein kinase with a compound of this invention (or its salt or prodrug) and monitoring the cells for any effect that the compound has on them. The effect may be any observable, either to the naked eye or through the use of instrumentation, change or absence of change in a cell phenotype. The change or absence of change in the cell phenotype monitored may be, for example, without limitation, a change or absence of change in the catalytic activity of the protein kinase in the cells or a change or absence of change in the interaction of the protein kinase with a natural binding partner.

Composition

Pharmaceutical compositions of the above compounds are a further aspect of this invention.

As used herein, the term "composition" is intended to encompass a product comprising the specified ingredients in the specified amounts, as well as any product which results, directly or indirectly, from combination of the specified ingredients in the specified amounts.

The present invention also encompasses a pharmaceutical composition useful in the treatment of cancer, comprising the administration of a therapeutically effective amount of the compounds of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate buryrate may be employed.

The compounds of the instant invention may also be co-administered with other well-known therapeutic agents that are selected for their particular usefuless against the condition that is being treated. For example, in the case of bone-related disorders, combinations that would be useful include those with antiresorptive bisphosphonates, such as alendronate and risedronate; integrin blockers (defined further below), such as $\alpha_v\beta_3$ antagonists; conjugated estrogens used in hormone replacement therapy, such as PREMPRO®, PREMARIN® and ENDOMEIRION®; selective estrogen receptor modulators (SERMs), such as raloxifene, droloxifene, CP-336,156 (Pfizer) and lasofoxifene; cathespin K inhibitors; and ATP proton pump inhibitors.

The instant compounds are also useful in combination with known anti-cancer agents. Such known anti-cancer agents include the following: estrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors, and other angiogenesis inhibitors. The instant compounds are particularly useful when coadminsitered with radiation therapy. The synergistic effects of inhibiting VEGF in combination with radiation therapy have been described in the art. (See WO 00/61186.)

"Estrogen receptor modulators" refers to compounds, which interfere or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenylhydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds, which interfere or inhibit the binding of retinoids to the receptor, regardless of mechanism. Examples of such retinoid receptor modulators include bexarotene, tretinoin, 13-cis-retinoic acid, 9-cis-retinoic acid, adifluoromethylornithine, ILX23-7553, trans-N-(4'-hydroxyphenyl) retinamide, and N4-carboxyphenyl retinamide.

"Cytotoxic agents" refer to compounds which cause cell death primarily by interfering directly with the cell's functioning or inhibit or interfere with cell myosis, including alkylating agents, tumor necrosis factors, intercalators, microtubulin inhibitors, and topoisomerase inhibitors.

Examples of cytotoxic agents include, but are not limited to, tirapazimine, sertenef, cachectin, ifosfamide, tasonermin, lonidamine, carboplatin, doxorubicin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidiumchloride, pumitepa, lobaplatin, satraplatin, profiromycin, cisplatin, irofulven, dexifosfamide, cis-aminedichloro(2-methyl-pyridine) platinum, benzylguanine, glufosfamide, GPX100, (trans, trans, trans)-bis-mu-(hexane-1,6-diamine)-mu-[diamine-platinum(II)]bis[diamine(chloro) platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, and 4-demethoxy-3-deamino-3-aziridinyl-4-methylsulphonyl-daunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, TDX258, and BMS 188797.

Some examples of topoisomerase inhibitors are topotecan, hycaptamine, irinotecan, rubitecan, 6-ethoxypropionyl-3',4'-O-exo-benzylidenechartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino] benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylaniino)ethyl)acridine-4-carboxamide, 6-[[2-(dimethylamino)ethyl]amino]-3-hydroxy-7H-indeno[2,1-c]quinolin-7-one, and dimesna.

"Antiproliferative agents" includes antisense RNA and DNA oligonucleotides such as G3139, ODN698, RVASKRAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannoheptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-

2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, and 3-aminopyridine-2-carboxaldehyde thiosemicarbazone. "Antiproliferative agents" also includes monoclonal antibodies to growth factors, other than those listed under "angiogenesis inhibitors", such as trastuzumab, and tumor suppressor genes, such as p53, which can be delivered via recombinant virus-mediated gene transfer (see U.S. Pat. No. 6,069,134, for example).

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include, but are not limited to, lovastatin (MEVACOR®, see U.S. Pat. Nos. 4,231,938, 4,294,926 and 4,319,039); simvastatin (ZOCOR®, see U.S. Pat. Nos. 4,444,784, 4,820,850 and 4,916,239); pravastatin (PRAVACHOL®, see U.S. Pat. Nos. 4,346,227, 4,537,859, 4,410,629, 5,030,447 and 5,180,589); fluvastatin (IESCOL®, see U.S. Pat. Nos. 5,354,772, 4,911,165, 4,929,437, 5,189,164, 5,118,853, 5,290,946 and 5,356,896); atorvastatin (LIPITOR®, see U.S. Pat. Nos. 5,273,995, 4,681,893, 5,489,691 and 5,342,952); and cerivastatin (also known as rivastatin and BAYCHOL®, see U.S. Pat. No. 5,177,080). The structural formulae of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

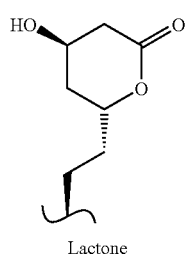

Lactone

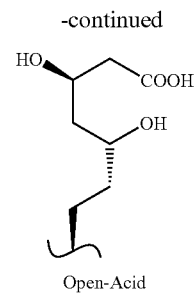

Open-Acid

In IMG-COA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenzimidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). Examples of prenyl-protein transferase inhibiting compounds include (±)-6-[amino(4-chlorophenyl)(1-methyl-1H-imidazol-5-yl) methyl]-4-(3-chlorophenyl)-1-methyl-2(1H)-quinolinone, (−)-6-[amino(4-chlorophenyl)(1-methyl-1H-imidazol-5-yl) methyl]-4-(3-chlorophenyl)-1-methyl-2(1H)-quinolinone, (+)-6-[amino(4-chlorophenyl)(1-methyl-1H-imidazol-5-yl) methyl]-4-(3-chlorophenyl)-1-methyl-2(1H)-quinolinone, 5(S)-n-butyl-1-(2,3-dimethylphenyl)4-[1-(4-cyanobenzyl)-

5-imidazolylmethyl]-2-piperazinone, (S)-1-(3-chlorophenyl)-4-[1-(4-cyanobenzyl)-5-imidazolylmethyl]-5-[2-(ethanesulfonyl)methyl)-2-piperazinone, 5(S)-n-Butyl-1-(2-methylphenyl)-4-[1-(4-cyanobenzyl)-5-imidazolylmethyl]-2-piperazinone, 1-(3-chlorophenyl)-4-[1-(4-cyanobenzyl)-2-methyl-5-imidazolylmethyl]-2-piperazinone, 1-(2,2-diphenylethyl)-3-[N-(1-(4-cyanobenzyl)-1H-imidazol-5-ylethyl)carbamoyl]piperidine, 4-{5-[4-hydroxymethyl-4-(4-chloropyridin-2-ylmethyl)-piperidine-1-ylmethyl]-2-methylimidazol-1-ylmethyl}benzonitrile, 4-{5-[4-hydroxymethyl-4-(3-chlorobenzyl)-piperidine-1-ylmethyl]-2-methylimidazol-1-ylmethyl}benzonitrile, 4-{3-[4-(2-oxo-2H-pyridin-1-yl)benzyl]-3H-imidazol-4-ylmethyl}benzonitrile, 4-{3-[4-(5-chloro-2-oxo-2H-[1,2']bipyridin-5'-ylmethyl]-3H-imidazol-4-ylmethyl}benzonitrile, 4-{3-[4-(2-oxo-2H-[1,2']bipyridin-5'-ylmethyl]-3H-imidazol-4-ylmethyl}benzonitrile, 4-[3-(2-oxo-1-phenyl-1,2-dihydropyridin-4-ylmethyl)-3H-imidazol-4-ylmethyl}benzonitrile, 18,19-dihydro-19-oxo-5H,17H-6,10:12,16-dimetheno-1H-imidazo[4,3-c][1,11,4]dioxaazacyclo-nonadecine-9-carbonitrile, (±)-19,20-dihydro-19-oxo-5H-18,21-ethano-12,14-etheno-6,10-metheno-22H-benzo[d]imidazo[4,3-k][1,6,9,12]oxatriazacyclooctadecine-9-carbonitrile, 19,20-dihydro-19-oxo-5H,17H-18,21-ethano-6,10:12,16-dimetheno-22H-imidazo[3,4-h][1,8,11,14]oxatriazacycloeicosine-9-carbonitrile, and (±)-19,20-dihydro-3-methyl-19-oxo-5H-18,21-ethano-12,14-etheno-6,10-metheno-22H-benzo [d]imidazo[4,3-k][1,6,9,12]oxa-triazacyclooctadecine-9-carbonitrile.

Other examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see European J. of Cancer, Vol. 35, No. 9, pp. 1394-1401 (1999).

Examples of HIV protease inhibitors include amprenavir, abacavir. CGP-73547, CGP-61755, DMP-450, indinavir, nelfinavir, tipranavir, ritonavir, saquinavir, ABT-378, AG 1776, and BMS-232,632. Examples of reverse transcriptase inhibitors include delaviridine, efavirenz, GS-840, HB Y097, lamivudine, nevirapine, AZT, 3TC, ddC, and ddI.

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR20), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxygenase-2 inhibitors like celecoxib and rofecoxib (PNAS, Vol. 89, p. 7384 (1992); JNCI, Vol. 69, p. 475 (1982); Arch. Opthalmol., Vol. 108, p. 573 (1990); Anat. Rec., Vol. 238, p. 68 (1994); FEBS Letters, Vol. 372, p. 83 (1995); Clin, Orthop. Vol. 313, p. 76 (1995); J. Mol. Endocrinol., Vol. 16, p. 107 (1996); Jpn. J. Pharmacol., Vol. 75, p. 105 (1997); Cancer Res., Vol. 57, p. 1625 (1997); Cell, Vol. 93, p. 705 (1998); Intl. J. Mol. Med., Vol. 2, p. 715 (1998); J. Biol. Chem., Vol. 274, p. 9116 (1999)), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., J. Lab. Clin. Med. 105:141-145 (1985)), and antibodies to VEGF. (see, Nature Biotechnology, Vol. 17, pp. 963-968 (October 1999); Kim et al., Nature, 362, 841-844 (1993); WO 00/44777; and WO 00/61186).

As described above, the combinations with NSAID's are directed to the use of NSAID's which are potent COX-2 inhibiting agents. For purposes of this specification an NSAID is potent if it possess an $IC_{50}$ for the inhibition of COX-2 of 1 μm or less as measured by the cell or microsomal assay disclosed herein.

The invention also encompasses combinations with NSAID's which are selective COX-2 inhibitors. For purposes of this specification NSAID's which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by the cell or microsomal assay disclosed hereinunder. Such compounds include, but are not limited to those disclosed in U.S. Pat. No. 5,474,995, issued Dec. 12, 1995, U.S. Pat. No. 5,861,419, issued Jan. 19, 1999, U.S. Pat. No. 6,001,843, issued Dec. 14, 1999, U.S. Pat. No. 6,020,343, issued Feb. 1, 2000, U.S. Pat. No. 5,409,944, issued Apr. 25, 1995, U.S. Pat. No. 5,436,265, issued Jul. 25, 1995, U.S. Pat. No. 5,536,752, issued Jul. 16, 1996, U.S. Pat. No. 5,550,142, issued Aug. 27, 1996, U.S. Pat. No. 5,604, 260, issued Feb. 18, 1997, U.S. Pat. No. 5,698,584, issued Dec. 16, 1997, U.S. Pat. No. 5,710,140, issued Jan. 20, 1998, WO 94/15932, published July 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932, 598, issued Aug. 3, 1999, all of which are hereby incorporated by reference.

Inhibitors of COX-2 that are particularly useful in the instant method of treatment are:

3-phenyl4-(4-(methylsulfonyl)phenyl)-2-(5H)-furanone; and

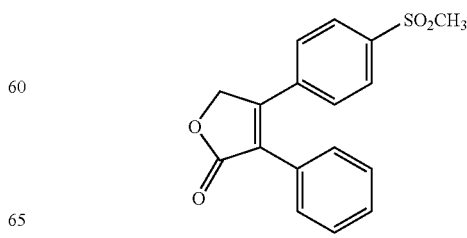

5-chloro-3-(4-methylsulfonyl)phenyl-2-(2-methyl-5-pyridinyl)pyridine;

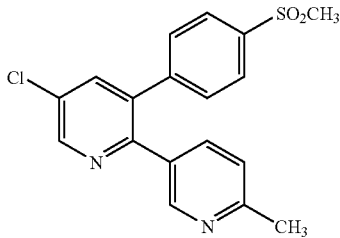

or a pharmaceutically acceptable salt thereof.

General and specific synthetic procedures for the preparation of the COX-2 inhibitor compounds described above are found in U.S. Pat. No. 5,474,995, issued Dec. 12, 1995, U.S. Pat. No. 5,861,419, issued Jan. 19, 1999, and U.S. Pat. No. 6,001,843, issued Dec. 14, 1999, all of which are herein incorporated by reference.

Compounds that have been described as specific inhibitors of COX-2 and are therefore useful in the present invention include, but are not limited to, the following:

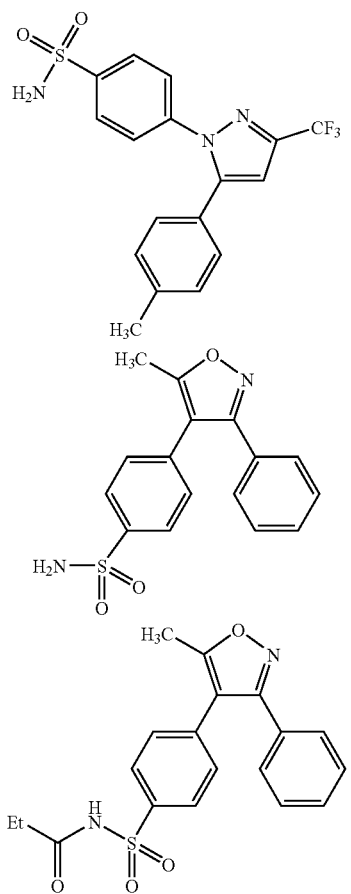

or a pharmaceutically acceptable salt thereof.

Compounds, which are described as specific inhibitors of COX-2 and are therefore useful in the present invention, and methods of synthesis thereof, can be found in the following patents, pending applications and publications, which are herein incorporated by reference: WO 94/15932, published Jul. 21, 1994, U.S. Pat. No. 5,344,991, issued Jun. 6, 1994, U.S. Pat. No. 5,134,142, issued Jul. 28, 1992, U.S. Pat. No. 5,380,738, issued Jan. 10, 1995, U.S. Pat. No. 5,393,790, issued Feb. 20, 1995, U.S. Pat. No. 5,466,823, issued Nov. 14, 1995, U.S. Pat. No. 5,633,272, issued May 27, 1997, and U.S. Pat. No. 5,932,598, issued Aug. 3, 1999.

Compounds which are specific inhibitors of COX-2 and are therefore useful in the present invention, and methods of synthesis thereof, can be found in the following patents, pending applications and publications, which are herein incorporated by reference: U.S. Pat. No. 5,474,995 issued Dec. 12, 1995, U.S. Pat. No. 5,861,419 issued Jan. 19, 1999, U.S. Pat. No. 6,001,843 issued Dec. 14, 1999, U.S. Pat. No. 6,020,343 issued Feb. 1, 2000, U.S. Pat. No. 5,409,944 issued Apr. 25, 1995, U.S. Pat. No. 5,436,265 issued Jul. 25, 1995, U.S. Pat. No. 5,536,752 issued Jul. 16, 1996, U.S. Pat. No. 5,550,142 issued Aug. 27, 1996, U.S. Pat. No. 5,604,260 issued Feb. 18, 1997, U.S. Pat. No. 5,698,584 issued Dec. 16, 1997, and U.S. Pat. No. 5,710,140 issued Jan. 20,1998.

Other examples of angiogenesis inhibitors include, but are not limited to, endostation, ukrain, ranpimase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide,CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha v\beta_6$, $\alpha v\beta_8$, $\alpha_1\beta_1$, $\alpha_2\beta_1$, $\alpha_5\beta_1$, $\alpha_6\beta_1$ and $\alpha_6\beta_4$ integrins. The term also refers to antagonists of any combination of $\alpha v\beta_3$, $\alpha v\beta_5$, $\alpha v\beta_6$, $\alpha v\beta_8$, $\alpha_1\beta_1$, $\alpha_2\beta_1$, $\alpha_5\beta_1$, $\alpha_6\beta_1$ and $\alpha_6\beta_4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

The instant compounds are also useful, alone or in combination with platelet fibrinogen receptor (GP IIb/IIIa) antagonists, such as tirofiban, to inhibit metastasis of cancerous cells. Tumor cells can activate platelets largely via thrombin generation. This activation is associated with the release of VEGF. The release of VEGF enhances metastasis by increasing extravasation at points of adhesion to vascular endothelium (Amirkhosravi, *Platelets* 10, 285-292, 1999). Therefore, the present compounds can serve to inhibit metastasis, alone or in combination with GP IIb/IIIa) antagonists. Examples of other fibrinogen receptor antagonists include abciximab, eptifibatide, sibrafiban, lamifiban, lotrafiban, cromofiban, and CT50352.

Formulations

The compounds of this invention may be administered to mammals, preferably humans, either alone or, preferably, in combination with pharmaceutically acceptable carriers, excipients or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and/or topical routes of administration.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

For oral use of a compound according to this invention, particularly for chemotherapy, the selected compound may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled .in order to render the preparation isotonic.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitan monooleate, or condensation products of ethylene oxide with partial esters derived from fatty acids and hexitol anhydrides, for example polyethylene sorbitan monooleate.

The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solution. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents, which have been mentioned above. The sterile injectable preparation may also be a sterile injectable solution or suspension in a non-toxic parenterally acceptable diluent or solvent, for example as a solution in 1,3-butane diol. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

Additionally, the compounds of the instant invention may be administered to a mammal in need thereof using a gel extrusion mechanism (GEM) device, such as that described in U.S. Pat. No. 4,976,697, filed on Dec. 11, 1990, which is hereby incorporated by reference.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer. Administration occurs in an amount between about 0.1 mg/kg of body weight to about 60 mg/kg of body weight per day, preferably of between 0.5 mg/kg of body weight to about 40 mg/kg of body weight per day.

The compounds of this invention may be prepared by employing reactions as shown in the following schemes, in addition to other standard manipulations that are known in the literature or exemplified in the experimental procedures. It should be noted that, for the sake of brevity, only one enantiomer from the ring expansion is illustrated in the following schemes. Substitutions on the benzazocine moiety A, as illustrated hereinabove, other than those specifically exemplified in the schemes, may be prepared using techniques known in the art or suitably substituted starting materials. These schemes, therefore, are not limited by the compounds depicted nor by any particular substituents employed for illustrative purposes. Substituent numbering, as shown in the schemes, does not necessarily correlate to that used in the claims.

It is understood that, in the below Schemes, R' represents —$(CR^{1a}{}_2)_{n-1}$—X—$(CR^{1a}{}_2)_p$—V—$(R^2)_q$ as defined in Formula I.

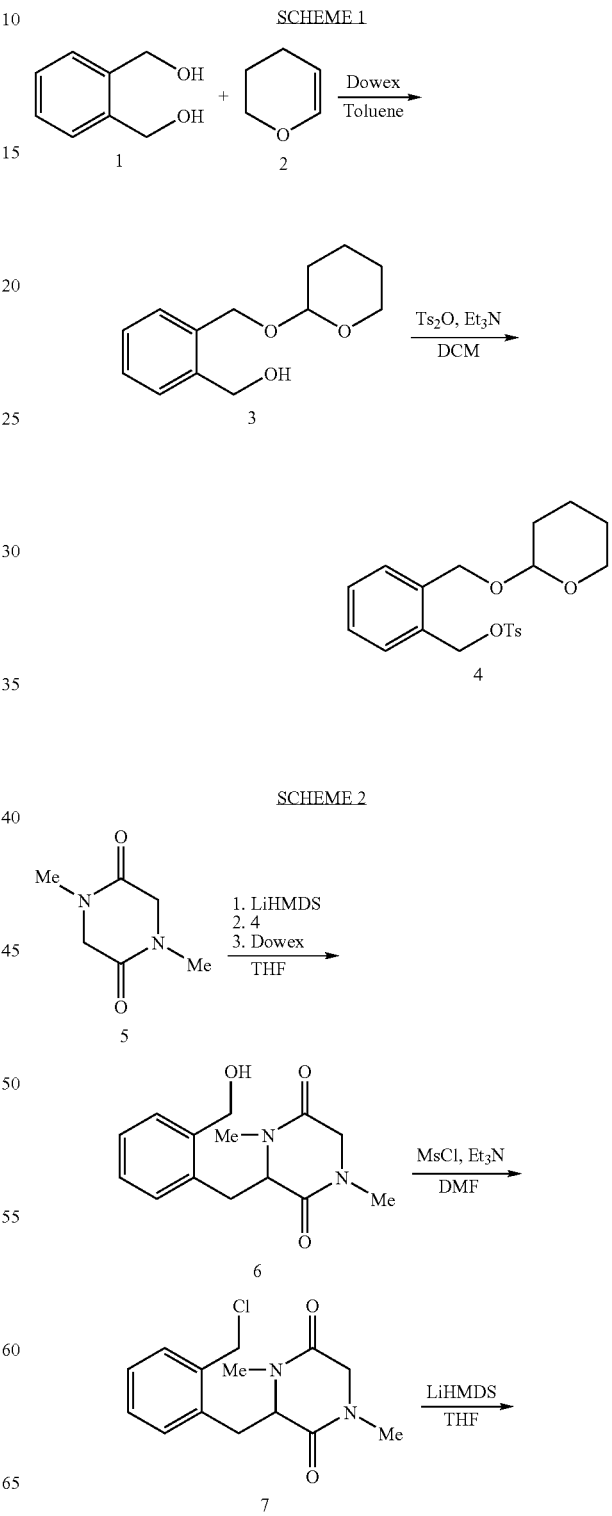

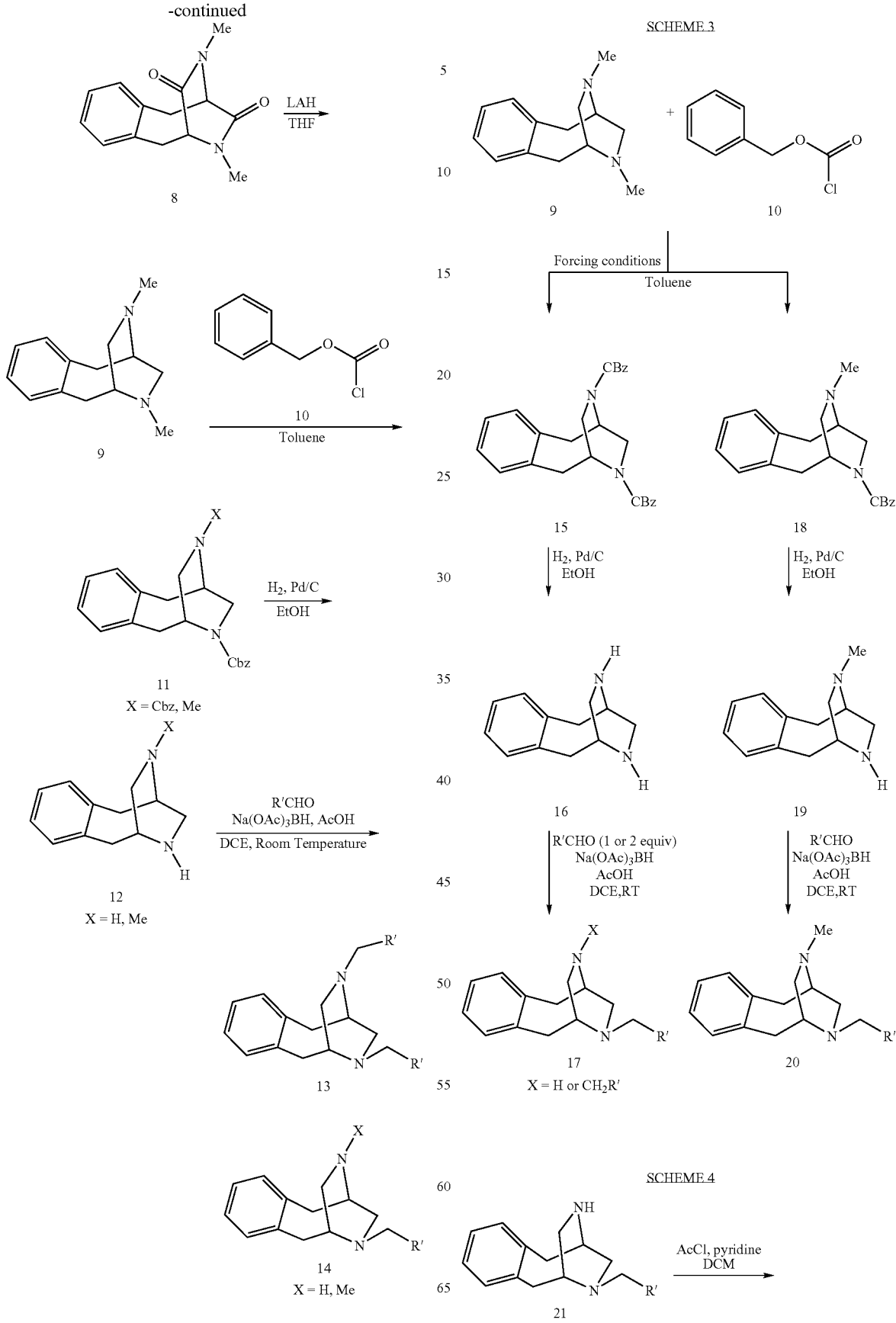

-continued

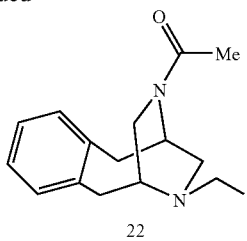

22

EXAMPLES

Examples provided are intended to assist in a further understanding of the invention. Particular materials employed, species and conditions are intended to be further illustrative of the invention and not limiting of the reasonable scope thereof.

Example 1

3-(3-bromobenzyl)-11-methyl-1,2,3,4,5,6-hexahydro-5,2-(epiminomethano)-3-benzazocinium dichloride

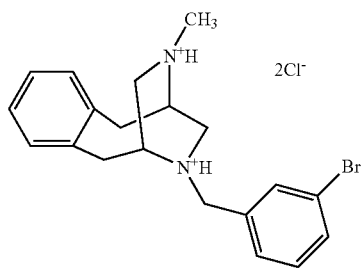

Step A: {2-[(tetrahydro-2H-pyran-2-yloxy)methyl]phenyl}methanol

To a suspension of 1,2-benzenedimethanol (5 g, 36.19 mmol) in toluene/2,3-dihydropyran (206 ml/11 ml) at 30° C. was added 3.62 g Dowex (50WX2-100). The reaction stirred at 30° C. for 5 hours. The mixture was filtered to remove Dowex, then concentrated in vacuo and put on vacuum pump overnight w/stirring to remove 2,3-dihydropyran. The crude reaction product was purified by normal phase chromatography (20% EtOAc/hexanes—25% -30%) to give a clear liquid (5.72 g).

Step B: 2-[(tetrahydro-2H-pyran-2-yloxy)methyl]benzyl 4-methylbenzenesulfonate

A solution of {2-[(tetrahydro-2H-pyran-2-yloxy)methyl]phenyl}methanol (5.52 g, 24.84 mmol) in CH$_2$Cl$_2$ (100 ml) was cooled to 0° C. and treated with Et$_3$N (6.92 ml, 49.68 mmol) followed by the addition of Ts$_2$O (8.9 g, 27.33 mmol). The reaction stirred at 0° C. for 3.5 hours. The mixture was diluted with sat. NH$_4$Cl and extracted with CH$_2$Cl$_{12}$ (2×). The combined organic solutions were washed with water, dried over Na$_2$SO$_4$ and concentrated in vacuo. The crude product was purified by normal phase chromatography (10% EtOAc/hexanes—20%) to give a light brown oil (7.36 g).

Step C: 3-[2-hydroxymethyl)benzyl]-1,4-dimethylpiperazine-2,5-dione

A solution of 1,4-dimethylpiperazine-2,5-dione (3.06 g, 21.51 mmol) in THF (100 ml) was cooled to −70° C. A LiHMDS solution (1 M, 23.46 mmol, 23.46 ml) was added via syringe and the reaction stirred for 15 minutes. A room temperature solution of 2-[(tetrahydro-2H-pyran-2-yloxy)methyl]benzyl 4-methylbenzenesulfonate (7.36 g, 19.55 mmol) in THF (30 mL) was added via cannula. The reaction stirred at −65° C. and allowed bath to melt for 9 hours. The mixture was quenched with sat. NH$_4$Cl and extracted with EtOAc (2×400 mL). Then combined organic solutions were washed with brine, dried over Na$_2$SO$_4$ and concentrated in vacuo. The reaction was purified by reverse phase HPLC and resulted in a mixture of protected/deprotected desired product. The mixture was partitioned between satd. NaHCO$_3$ and CH$_2$Cl$_2$ and extracted with CH$_2$Cl$_2$ (2×). The combined organic solutions were dried over Na$_2$SO$_4$ and concentrated to give 2.02 g of a pale yellow solid which contained both protected/deprotected desired product. The aqueous layer was extracted with CH$_2$Cl$_2$ and CHCl$_3$ (5×). The combined organic solutions were dried over Na$_2$SO$_4$ and concentrated to give 449 mg of desired product. The mixture of protected/deprotected desired product was dissolved in 90 ml of MeOH and treated with 2 g Dowex (50WX2-100). The solution stirred at ambient temperature for 5 hours. The reaction was filtered, rinsed with MeOH, and concentrated to give the desired product (1.48 g).

Step D: 2-[(1,4-dimethyl-3,6-dioxopiperazin-2-yl)methyl]benzyl chloride

A solution of 3-[2-(hydroxymethyl)benzyl]-1,4-dimethylpiperazine-2,5-dione (1.48 g, 5.64 mmol) and Et$_3$N (1.57 ml, 11.28 mmol) in DMF was cooled to 0° C. Mesyl chloride was added via syringe at 0° C. and the stirring reaction allowed to warm to ambient temperature via bath melting overnight. More Et$_3$N (2 equivalents) and mesyl chloride (1.1 equivalents) was added at 0° C. and the stirring reaction allowed to warm to ambient temperature via bath melting for 6 hours. LiCl (478 mg, 11.28 mmol) was added and the reaction stirred at ambient temperature for 1.5 hours. The mixture was partitioned between NH$_4$Cl and EtOAc and extracted with EtOAc (3×). The combined organic solutions were washed with brine, dried over Na$_2$SO$_4$ and concentrated. The crude product was purified by normal phase chromatography (0-3% MeOH(NH$_3$)/CH$_2$Cl$_2$) to give a yellow oil (1.47 g).

Step E: 3,11-dimethyl-2,3,5,6-tetrahydro-5,2-(epiminomethano)-3-benzazocine4,12(1H)-dione A solution of 2-[(1,4-dimethyl-3,6-dioxopiperazin-2-yl)methyl]benzyl chloride (1.47 g, 5.24 mmol) in THF (52 ml) was cooled to −65° C. LiHMDS (1M, 5.76 mmol, 5.76 ml) was added to the solution via syringe to give a yellow suspension. The reaction stirred for 2.5 hours and was allowed to warm up to −30° C. The mixture was quenched with sat. NH4Cl and extracted with EtOAc (3×). The combined organic solutions were washed with brine, dried over Na$_2$SO$_4$ and concentrated in vacuo. The crude reaction product was purified by normal phase chromatography (0-6% MeOH/CH$_2$Cl$_2$) to give a white solid (0.678 g).

Step F: 3,11-dimethyl-1,2,3,4,5,6-hexahydro-5,2-(epiminomethano)-3-benzazocine

A suspension of 3,11-dimethyl-2,3,5,6-tetrahydro-5,2-(epiminomethano)-3-benzazocine-4,12(1H)-dione (647 mg, 2.65 mmol) in THF (26 ml) was treated with LAH (1M, 10.59 mmol, 10.59 ml) and heated to reflux for 3 hours. The reaction cooled to ambient temperature and was then quenched with Na$_2$SO$_4$-decahydrate. The mixture was filtered, rinsed thoroughly with THF, and concentrated to give a clear oil (0.566 g).

Step G: benzyl 11-methyl-1,4,5,6-tetrahydro-5,2-(epiminomethano)-3-benzazocine-3(2H)-carboxylate A solution of 3,11-dimethyl-1,2,3,4,5,6-hexahydro-5,2-(epiminomethano)-3-benzazocine (92 mg, 0.425 mmol) in toluene (5 ml) was treated with benzyl chloroformate (1.4 mmol, 200 µl) and heated to 85° C. The reaction was stirred overnight. An additional 0.070 mL of benzyl chloroformate was added to the mixture and stirred at reflux for 5 hours. The reaction was cooled to ambient temperature and partitioned between satd. aqueous NaHCO$_3$ and EtOAc. The aqueous layer was washed with EtOAc. The organic solution was washed with brine, dried over Na$_2$SO$_4$ and concentrated in vacuo. The crude product was purified by normal phase chromatography (0-6% MeOH(NH$_3$)/CH$_2$Cl$_2$) to give a light brown oil (69 mg).

Step H: 3-methyl-1,2,3,4,5,6-hexahydro-5,2-(epiminomethano)-3-benzazocine

A solution of benzyl 11-methyl-1,4,5,6-tetrahydro-5,2-(epiminomethano)-3-benzazocine-3(2H)-carboxylate (69 mg, 0.205 mmol) in EtOH (4 ml) was treated with a slurry of Pd/C (11 mg) in EtOH. The reaction was purged briefly with H$_2$, then stirred under an H$_2$ balloon for 2 hours. The mixture was purged with Ar, then filtered through celite, rinsing thoroughly with EtOH. The reaction was concentrated in vacuo to give a clear oil (38 mg).

Step I: 3-(3-bromobenzyl)-11-methyl-1,2,3,4,5,6-hexahydro-5,2-(epiminomethano)-3-benzazocinium dichloride To a solution of 0.038 g of 3-methyl-1,2,3,4,5,6-hexahydro-5,2-(epiminomethano)-3-benzazocine (0.188 mmol) in 2 mL of DCE was added 0.02 mL of 3-bromobenzaldehyde (0.21 mmol) and 0.056 g Na(OAc)BH$_3$ (0.26 mmol). The resultant rnixture was stirred at ambient temperature under N$_2$ overnight, then poured into saturated aqueous sodium bicarbonate and extracted with CH2Cl2 (2×). The organic solutions were dried over Na$_2$SO$_4$, filtered, and purified by flash chromatography (0% -10% MeOH/CH$_2$Cl$_2$) to give a pale yellow oil (57 mg). $^1$H NMR (500 MHz , CDCl$_3$) δ 7.28 (br d, J=8 Hz, 1 H); 7.21-7.15 (m, 2H); 7.08-7.00 (m, 4H); 6.83 (br d, J=8 Hz, 1H); 3.49 (d, J=14 Hz, 1 H); 3.45 (d, J=14 Hz, 1 H); 3.22-3.16 (m, 3H); 3.10 (dd, J=15, 3 Hz, 1H); 3.03-2.97 (m, 2H); 2.91 (dd, J=11, 3 Hz, 1H); 2.86 (dd, J=11, 5 Hz, 1H); 2.78 (d, J=10 Hz, 1H); 2.59 (dd, J=11, 1 Hz, 1H); 2.45 (s, 3H). The bis-HCl salt of the compound was formed by exposure to excess HCl. HRMS (ES) exact mass calculated for C$_{20}$H$_{24}$BrN$_2$ (M+H$^+$): 371.1118. Found 371.1117.

Example 2

3-(3-bromobenzyl)-1,2,3,4,5,6-hexahydro-5,2-(epiminomethano)-3-benzazocinium dichloride

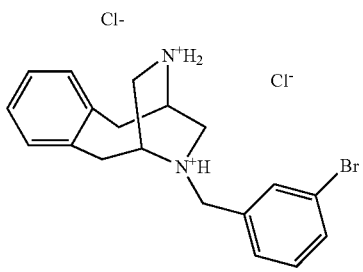

Step A: dibenzyl 1,4,5,6-tetrahydro-5,2-(epiminomethano)-3-benzazocine-3,11 (2H)-dicarboxylate A solution of 3,11-dimethyl-1,2,3,4,5,6-hexahydro-5,2-(epiminomethano)-3-benzazocine (51 mg, 0.236 mmol), prepared following the procedures described in Example 2 (Steps A-F) in toluene (4 ml) was treated with benzyl chloroformate (130 µL, 0.94 mmol) and heated at reflux. Only 85% conversion to mono-exchange product after stirring for 2.5 days. An additional 0.260 ml of benzyl chloroformate was added to the reaction and continued heating at reflux for 24 hours. Significant progress to presumed desired product (2:1 mono: di-Cbz). An additional 0.300 mL of benzyl chloroformate (4x) was added to the refluxing reaction over a course of 6 days. The mixture was cooled to ambient temperature and partitioned between satd. aqueous NaHCO$_3$ and EtOAc. The aqueous layer was extracted with EtOAc (1×). The organic layer was washed with brine, dried over Na$_2$SO$_4$ and concentrated in vacuo. The crude product was purified by normal phase chromatography (0-3-6% MeOH(NH$_3$)/CH$_2$Cl$_2$) to give a light brown foam (70 mg).

Step B: 1,2,3,4,5,6-hexahydro-5,2-(epiminomethano)-3-benzazocine

A solution of dibenzyl 1,4,5,6-tetrahydro-5,2-(epiminomethano)-3-benzazocine-3,11(2H)-dicarboxylate (63 mg, 0.138 mmol) in EtOH (4 ml) was treated with a slurry of Pd/C (15 mg) in EtOH. The reaction was purged briefly with H$_2$, then stirred under an H$_2$ balloon for 2.5 hours. The mixture was purged with Ar, then filtered through celite, rinsing thoroughly with EtOH. The reaction was concentrated in vacuo to give a clear oil (27 mg).

Step C: 3-(3-bromobenzyl)-1,2,3,4,5,6-hexahydro-5,2-(epiminomethano)-3-benzazocinium dichloride Following the procedures described in Example 1, replacing 3-methyl-1,2,3,4,5,6-hexahydro-5,2-(epiminomethano)-3-benzazocine in Step I with 1,2,3,4,5,6-hexahydro-5,2-(epiminomethano)-3-benzazocine and using a single equivalent of 3-bromobenzaldehyde, the title compound was obtained. $^1$H NMR (500 MHz, CDCl$_3$) δ 7.37-7.35 (m, 1 H); 7.33 (br s, 1H); 7.22-7.18 (m, 2H); 7.16-7. m, 4H); 3.81-378 (m, 1H); 3.75 (d, J=14 Hz, 1 H); 3.65 (d, J=14 Hz, 1H); 3.52 (dd, J=14, 6 Hz, 1H); 3.35 (dd, J=13, 4 Hz, 1H); 3.21-3.20 (m, 1H); 3.08-3.03 (m, 2H); 2.97 (dd, J=11, 4 Hz, 1H); 2.94 (dd, J=16, 7 Hz, 1H); 2.89-2.84 (m, 2H). The bis-HCl salt of the compound was formed by exposure to excess HCl. HRMS (ES) exact mass calculated for C$_{19}$H$_{22}$BrN$_2$ (M+H$^+$): 357.0461. Found 357.0955.

Example 3

3,11-bis(3-bromobenzyl)-1,2,3,4,5,6-hexahydro-5,2-(epiminomethano)-3-benzazocinium dichloride

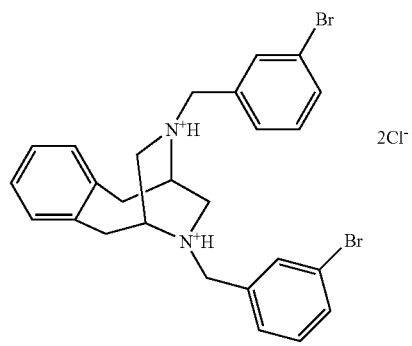

Following the procedures described in Example 1, replacing 3-methyl-1,2,3,4,5,6-hexahydro-5,2-(epiminomethano)-3-benzazocine in Step I with 1,2,3,4,5,6-Hexahydro-5,2-(epiminomethano)-3-benzazocine and using two equivalents of 3-bromobenzaldehyde, the title compound was obtained. $^1$H NMR (500 MHz, CDCl$_3$) δ7.32 (br d, J=8 Hz, 2 H); 7.21-7.18 (m, 2H); 7.16 (br s, 2 H); 7.09 (t, J=8 Hz, 2H); 7.05-7.03 (m, 2H); 6.97 (br d, J=8 Hz, 2H); 3.62 (d, J=14 Hz, 1 H);3.58(d, J=14 Hz, 1 H);3.20(m, 2 H);3.13 (dd, J=14,6 Hz, 2H);2.98 (dd, J=14, 6 Hz, 2H); 2.85 (dd, J=11, 3 Hz, 2H); 2.73 (d, J=10 Hz, 2H). The bis-HCl salt of the compound was formed by exposure to excess HCl. HRMS (ES) exact mass calculated for C$_{26}$H$_{27}$Br$_2$N$_2$ (M+H$^{30}$ ): 525.0536. Found 525.0526.

Example 4

11-acetyl-3-(3-bromobenzyl)-1,2,3,4,5,6-hexahydro-5,2-(epiminomethano)-3-benzazocinium trifluoroacetate

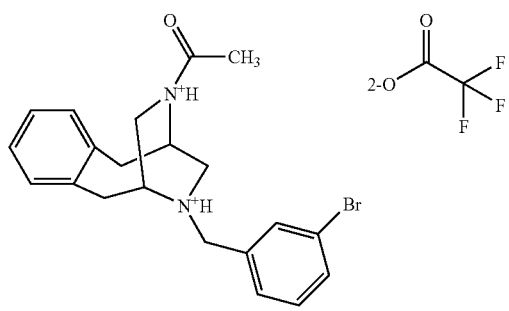

A solution of 3-(3-bromobenzyl)-1,2,3,4,5,6-hexahydro-5,2-(epiminomethano)-3-benzazocinium dichloride (26 mg, 0.138 mmol), prepared following the procedures described in Example 2, in CH$_2$Cl$_2$ (2 ml) was treated with pyridine (0.19 mmol, 20 μl) and acetyl chloride (0.09 mmol, 10 μl). The reaction stirred at ambient temperature for 2.5 hours. The mixture was diluted with EtOH and concentrated in vacuo. The residue was taken up in acetonitrile and purified by reverse phase HPLC to give a white powder. $^1$H NMR (500 MHz, CD$_3$OD) δ 7.82 (d, J=11 Hz, 1H); 7.68 (d, J=8 Hz, 1 H); 7.58 (t, J=9 Hz, 1 H); 7.44 (t, J=8 Hz, 1 H); 7.22-7.15 (m, 3H); 7.07 (d, J=8 Hz, 1 H); 4.90 (m, 1 H); 4.67 (br, 1H); 3.90 (br d, J=12 Hz, 1 H); 3.69-3.33 (m, 6H); 3.27-3.24 (m, 1H); 3.14 (dd, J=15, 8 Hz, 1H); 1.50 (s, 3 H). HRMS (ES) exact mass calculated for C$_{21}$H$_{24}$BrN$_2$O (M+H$^+$): 399.1067. Found 399.1073.

Example 5

The salt compounds prepared above may be neutralized using techniques know in the art. For example, the salt may be treated with a suitable dilute aqueous base solution such as dilute aqueous NaOH, potassium carbonate, ammonia and sodium bicarbonate to produce the free form, or non-salt form, of the compound. Listed below is the free form name for the corresponding salt compound described in the example recited:

| Example | Free Form Name |
| --- | --- |
| 1 | 3-(3-bromobenzyl)-11-methyl-1,2,3,4,5,6-hexahydro-5,2-(epiminomethano)-3-benzazocine |
| 2 | 3-(3-bromobenzyl)-1,2,3,4,5,6-hexahydro-5,2-(epiminomethano)-3-benzazocine |
| 3 | 3,11-bis(3-bromobenzyl)-1,2,3,4,5,6-hexahydro-5,2-(epiminomethano)-3-benzazocine |
| 4 | 11-acetyl-3-(3-bromobenzyl)-1,2,3,4,5,6-hexahydro-5,2-(epiminomethano)-3-benzazocine |

Assays

The compounds of the instant invention described in the Examples above were tested by the assays described below and were found to have kinase inhibitory activity. In particular, the compounds of the instant invention inhibited IGF-1R or insulin receptor kinase activity with an IC$_{50}$ of less than or equal to about 100 μM. Other assays are known in the literature and could be readily performed by those with skill in the art (see for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

IGF-1R Kinase Assay

IGF-1R receptor kinase activity is measured by incorporation of phosphate into a peptide substrate containing a tyrosine residue. Phosphorylation of the peptide substrate is quantitated using anti-IGF-1R and anti-phosphotyrosine antibodies in an HTRF (Homogeneous Time Resolved Fluorescence) detection system. (Park, Y-W., et al. Anal. Biochem., (1999) 269, 94-104)

Material

IGF-1R Receptor Kinase Domain

The intracellular kinase domain of human IGF-1R was cloned as a glutathione S-transferase fusion protein. IGF-1R β-subunit amino acid residues 930 to 1337 (numbering system as per Ullrich et al., EMBO J. (1986) 5, 2503-2512) were cloned into the baculovirus transfer vector pAcGHLT-A (BD-Pharmingen) such that the N-terminus of the IGF-1R residues are fused to the C-terminus of the GST domain encoded in the transfer vector pAcGHLT-A. Recombinant virus was generated and the fusion protein expressed in SF-9 insect cells (BD-Pharmingen). Enzyme was purified by means of a glutathione sepharose column.

Insulin Receptor Kinase Domain

The intracellular kinase domain of human insulin receptor was cloned as a glutathione S-transferase fusion protein. Insulin receptor β-subunit amino acid residues 941 to 1343 (numbering system as per Ullrich et al., Nature, (1985) 313, 756-761) were cloned into the baculovirus transfer vector pAcGHLT-A (BD-Pharrningen) such that the N-terminus of the IGF-1R residues are fused to the C-terminus of the GST domain encoded in the transfer vector pAcGHLT-A. Recombinant virus was generated and the fusion protein expressed in SF-9 insect cells (BD-Pharmingen) Enzyme was purified by means of a glutathione sepharose column.

Insect Cell Lysis Buffer 10 mM Tris pH 7.5; 130 mM NaCl; 2 mM DTT; 1% Triton X-100; 10 mM NaF; 10 mM NaPi; 10 mM NaPPi; 1× protease inhibitor cocktail (Pharmingen).

Wash Buffer

Phosphate Buffered Saline (PBS): 137 Mm NaCl, 2.6 mM KCl, 10 mM $Na_2HPO_4$, 1.8 mM $KH_2PO_4$, pH 7.4; 1 mM DTT; 1× protease inhibitor cocktail Dialysis Buffer 20 mM Tris pH 7.5; 1 mM DTT; 200 mM NaCl; 0.05% Triton X-100 and 50% glycerol Enzyme Dilution Buffer 50 mM Tris pH 7.5; 1 mM DTT; 100 mM NaCl; 10% glycerol; 1 mg/ml BSA Enzyme Reaction Buffer 20 mM Tris pH 7.4; 100 mM NaCl; 1 mg/ml BSA; 5 mM $MgCl_2$; 2 mM DTT Quench Buffer 125 mM Tris pH 7.8; 75 mM EDTA; 500 mM KF; 0.125% Triton X-100; 1.25% BSA; 60 nM SA-XL665 (Packard); 300 pM europium cryptate labeled anti-phosphotyrosine antibody (Eu-PY20)

Peptide Substrate

Sequence LCB-EQEDEPEGDYFEWLE-$NH_2$; stock solution is 1 mM disolved in DMSO; diluted to 1 uM in 1× enzyme reaction buffer for 10× working stock. (LCB=aminohexanoylbiotin)

ATP

Stock solution is 0.5 M ATP (Boehringer) pH 7.4; stock solution is diluted to 40 mM ATP in enzyme reaction buffer to give 20× working stock solution.

HEK-21 Cell Line

Human embryonic kidney cells (HEK-293) (ATCC) were transfected with an expression plasmid containing the entire IGF-1R coding sequence. After antibiotic selection, colonies were screened for IGF-1R overexpression by western blot analysis. One clone, designated HEK-21 was selected for cell based IGF-1R autophosphorylation assays.

HEK Cell Growth Media

Dulbecco's Modified Eagle's Media (DMEM), 10% Fetal Calf Serum, 1× Penn/Strep, 1× Glutamine, 1× Non-essential amino acids (all from Life Technologies)

Cell Lysis Buffer 50 mM Tris-HCl pH 7.4; 150 mM NaCl; 1% Triton X-100 (Sigma); 1× Mammalian protease inhibitors (Sigma); 10 mM NaF; 1 mM NaVanadate Western Blocking Buffer 20 mM Tris-HCl pH 8.0; 150 mM NaCl; 5% BSA (Sigma); 0.1% Tween 20 (Biorad)

Methods

A. Protein Purification

*Spodoptera frugiperda* SF9 cells were transfected with recombinant virus encoding either the GST-IGF-1R β-subunit or GST-InsR fusion protein at an MOI of 4 virus particles/cell. Cells are grown for 48 hours at 27° C., harvested by centrifugation and washed once with PBS. The cell pellet is frozen at −70° C. after the final centrifugation. All subsequent purification steps are performed at 4° C. 10 grams of frozen cell paste is thawed in a 90 ml volume of insect cell lysis buffer (BD-Pharmingen) and held on ice with occasional agitation for 20 minutes. The lysate is centrifuged at 12000 g to remove cellular debris. Lysis supernatant was mixed with 45 ml of glutathione agarose beads (BD-Pharmingen) and agitated slowly at 4° C. for one hour after which the beads were centrifuged and washed 3× with wash buffer. The beads are resuspended in 45 ml of wash buffer and poured as a slurry into a chromatography column. The column is washed with 5 volumes of wash buffer and the GST-IGF-1R is eluted from the column with 5 mM Glutathione in wash buffer. Pooled fractions are dialyzed vs. dialysis buffer and stored at −20° C.

B. IGF-1R Kinase Assay

The IGF-1R enzyme reaction is run in a 96 well plate format. The enzyme reaction consists of enzyme reaction buffer plus 0.1 nM GST-IGF-1R, 00 nM peptide substrate and 2 mM ATP in a final volume of 60 microliters. Inhibitor, in DMSO, is added in a volume 1 microliter and preincubated for 10 minutes at 22° C. Final inhibitor concentration can range from 100 uM to 1 nM. The kinase reaction is initiated with 3 microliters of 40 mM ATP. After 20 minutes at 22° C., the reaction is stopped with 40 microliters of quench buffer and allowed to equilibrate for 2 hours at 22° C. Relative fluorescent units are read on a Discovery plate reader (Packard). IC50s for compounds are determined by 4 point sigmoidal curve fit.

C. Insulin Receptor Kinase Assay

The kinase reaction for insulin receptor is identical to that used to assay IGF-1R (above), except that GST-InsR is substituted at a final concentration of 0.1 nM.

D. Cell Based IGF-1R Autophosphorylation Assay

IGF-1R inhibitor compounds are tested for their ability to block IGF-I induced IGF-1R autophosphorylation in a IGF-1R transfected human embryonic kidney cell line (HEK-21). HEK-21 cells over-expressing the human IGF-1R receptor are cultured in 6-well plates (37° C. in a 5% $CO_2$ atmosphere) in HEK cell growth media to 80% of confluence. Cells are serum starved for four hours in HEK growth media with 0.5% fetal calf serum. A 10× concentration of inhibitor in growth media is added to the cells in one-tenth the final media volume and allowed to preincubate for one hour at 37° C. Inhibitor concentration can range from 10 nM to 100 uM. IGF-I (Sigma) is added to the serum starved cells to a final concentration of 30 ng/ml. After a 10 minute incubation in the presence of IGF-I at 37° C., the media is removed, the cells washed once with PBS and 0.5 mls of cold cell lysis buffer added. After 5 minutes incubation on ice, cells are scraped from the wells and lysis buffer plus cells are transferred to a 1.5 ml microfuge tube. The total lysate is held at 4° C. for twenty minutes and then centrifuged at top speed in a microfuge. The supernatant is removed and saved for analysis. Phosphorylation status of the receptor is assessed by Western blot. Lysates are electrophoresed on 8% denaturing Tris-Glycine polyacrylamide gels and the proteins transferred to nitrocellulose filters by electro-blotting. The blots are blocked with blocking reagent for 10 minutes after which anti-phosphotyrosine antibody (4G10, Upstate Biotechnology) is added to a final dilution of 1:1500. Blots and primary antibody are incubated at 4° C. overnight. After washing with PBS plus 0.2% Tween 20 (Biorad), an HRP conjugated anti-mouse secondary antibody (Jackson Labs) is added at a dilution of 1:15000 and incubated at 4° C. for 2 hours. Blots are then washed with PBS-Tween and developed using ECL (Amersham) luminescent reagent. Phosphorylated IGF-1R on the blots is visualized by autoradiography or imaging using a Kodak Image Station 440. IC50s are determined through densitometric scanning or quantitation using the Kodak Digital Science software.

What is claimed is:

1. A compound of Formula II

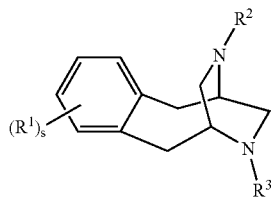

wherein:

$R_1$ is independently selected from
1) H,
2) halo,
3) $OR^4$,
4) $NO_2$,
5) $—S(O)_m R^4$,
6) CN
7) unsubstituted or substituted $C_1$-$C_{10}$ alkyl,
8) unsubstituted or substituted aryl,
9) unsubstituted or substituted $C_2$-$C_6$ alkenyl,
10) unsubstituted or substituted $C_3$-$C_{10}$ cycloalkyl,
11) unsubstituted or substituted $C_2$-$C_6$ alkynyl,
12) unsubstituted or substituted heterocycle,
13) $—C(O)R^4$,
14) $C(O)OR^4$,
15) $C(O)N(R^4)_2$,
16) $S(O)_m N(R^4)_2$, and
17) $N(R^4)_2$;

$R^2$ is selected from
1) H,
2) $C_1$-$C_6$ alkyl, and
3) $(C=O)C_1$-$C_6$ alkyl,
wherein said alkyl is optionally substituted with phenyl wherein said phenyl is optionally substituted with halo;

$R^3$ is
1) $C_1$-$C_6$ alkyl
wherein said alkyl is optionally substituted with phenyl wherein said phenyl is optionally substituted with halo;

$R^4$ is independently selected from
1) H,
2) unsubstituted or substituted $C_{1-10}$ alkyl,
3) unsubstituted or substituted $C_3$-$C_{10}$ cycloalkyl,
4) unsubstituted or substituted aryl,
5) unsubstituted or substituted heterocycle, and
6) $CF_3$;

m is independently 0, 1 or 2;

s is 1 to 4;

or a pharmaceutically acceptable salt or stereoisomer thereof.

2. A pharmaceutical composition which is comprised of a compound in accordance with claim 1 and a pharmaceutically acceptable carrier.

3. A compound that is
3-(3-bromobenzyl)-11-methyl-1,2,3,4,5,6-hexahydro-5,2-(epiminomethano)-3-benzazocine;
3-(3-bromobenzyl)-1,2,3,4,5,6-hexahydro-5,2-(epiminomethano)-3-benzazocine;
3,11-bis(3-bromobenzyl)-1,2,3,4,5,6-hexahydro-5,2-(epiminomethano)-3-benzazocine;
11-acetyl-3-(3-bromobenzyl)-1,2,3,4,5,6-hexahydro-5,2-(epiminomethano)-3benzazocine;
or a pharmaceutically acceptable salt or stereoisomer thereof.

4. A method of treating gliomas, meningomas, colon cancer, gastric cancer, pancreatic cancer, esophageal cancer, hepatocellular cancer, lung (small cell and non-small cell) cancer, thyroid cancer, breast cancer, ovarian cancer, endometrial cancer, vaginal cancer, cervical cancer, prostate cancer, testicular cancer, renal cell cancer, bladder cancer, osteosarcoma, chondrosarcoma, melanoma, basal cell carcinoma, Hodgkin's disease and retinal vascularization in a mammal in need of such treatment comprising administering to said mammal a therapeutically effective amount of a compound of claim 1.

* * * * *